(12) United States Patent
Schumacher et al.

(10) Patent No.: US 11,702,938 B2
(45) Date of Patent: Jul. 18, 2023

(54) ROTOR FOR A PUMP, PRODUCED WITH A FIRST ELASTIC MATERIAL

(71) Applicant: ECP Entwicklungsgesellschaft MBH, Aachen (DE)

(72) Inventors: Joerg Schumacher, Aachen (DE); Mario Scheckel, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 0 days.

(21) Appl. No.: 17/696,977

(22) Filed: Mar. 17, 2022

(65) Prior Publication Data
US 2022/0316340 A1    Oct. 6, 2022

Related U.S. Application Data

(63) Continuation of application No. 16/748,152, filed on Jan. 21, 2020, now Pat. No. 11,313,228, which is a (Continued)

(30) Foreign Application Priority Data

Jul. 15, 2010    (EP) .................................. 10075303

(51) Int. Cl.
    *F04D 29/18*        (2006.01)
    *F04D 29/02*        (2006.01)
    (Continued)

(52) U.S. Cl.
    CPC .............. *F01D 5/02* (2013.01); *A61M 60/122* (2021.01); *A61M 60/13* (2021.01); (Continued)

(58) Field of Classification Search
    CPC .............. F04D 3/02; F04D 7/00; F04D 29/18; F04D 29/181; F04D 29/183; F04D 29/026
    See application file for complete search history.

(56) References Cited

U.S. PATENT DOCUMENTS 2,533,716 A    12/1950   Ray
3,333,127 A    7/1967    Congdon et al.
(Continued)

FOREIGN PATENT DOCUMENTS

CA    1008330 A     4/1977
CA    2311977 A1    12/2000
(Continued)

OTHER PUBLICATIONS

Brandel, et al., "Negative Poisson's ratio polyethylene forams," Journal of Materials Science, vol. 36: 5885-5893 (2001).
(Continued)

*Primary Examiner* — Deming Wan
(74) *Attorney, Agent, or Firm* — Botos Churchill IP Law LLP

(57) ABSTRACT

A rotor for a pump has a housing and a rotor, and has at least one blade. The rotor is able to be actuated to rotate about an axis of rotation in order to convey a fluid in the axial or radial direction, and the rotor is able to be deformed in the radial direction between a first, radially compressed state and a second, radially expanded state. At a maximum speed of rotation of the rotor at which the power of the pump is at a maximum, the blade is essentially radially oriented, and/or the rotor has its maximum diameter.

5 Claims, 15 Drawing Sheets

Related U.S. Application Data continuation of application No. 15/671,326, filed on Aug. 8, 2017, now Pat. No. 10,584,589, which is a continuation of application No. 13/261,565, filed as application No. PCT/EP2011/003440 on Jul. 1, 2011, now Pat. No. 9,771,801.

(60) Provisional application No. 61/364,578, filed on Jul. 15, 2010.

(51) Int. Cl.

| | | |
|---|---|---|
| *F04D 7/00* | (2006.01) | |
| *F01D 5/02* | (2006.01) | |
| *A61M 60/411* | (2021.01) | |
| *A61M 60/13* | (2021.01) | |
| *A61M 60/226* | (2021.01) | |
| *A61M 60/237* | (2021.01) | |
| *A61M 60/808* | (2021.01) | |
| *A61M 60/122* | (2021.01) | |
| *A61M 60/135* | (2021.01) | |
| *A61M 60/205* | (2021.01) | |
| *A61M 60/148* | (2021.01) | |
| *A61M 60/414* | (2021.01) | |

(52) U.S. Cl.
CPC ........ *A61M 60/135* (2021.01); *A61M 60/205* (2021.01); *A61M 60/226* (2021.01); *A61M 60/237* (2021.01); *A61M 60/411* (2021.01); *A61M 60/808* (2021.01); *A61M 60/148* (2021.01); *A61M 60/414* (2021.01)

(56) References Cited

U.S. PATENT DOCUMENTS

| | | |
|---|---|---|
| 3,354,833 A | 11/1967 | Laing |
| 3,489,145 A | 1/1970 | Judson et al. |
| 3,510,229 A | 5/1970 | Smith |
| 3,568,659 A | 3/1971 | Karnegis |
| 3,802,551 A | 4/1974 | Somers |
| 3,812,812 A | 5/1974 | Hurwitz |
| 3,846,045 A | 11/1974 | Mincuzzi |
| 3,936,683 A | 2/1976 | Walker |
| 4,014,317 A | 3/1977 | Bruno |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,207,028 A | 6/1980 | Ridder |
| 4,420,851 A | 12/1983 | Wiener |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier et al. |
| 4,801,243 A | 1/1989 | Norton |
| 4,957,504 A | 9/1990 | Chardack |
| 4,969,865 A | 11/1990 | Hwang et al. |
| 4,984,972 A | 1/1991 | Clausen et al. |
| 4,995,857 A | 2/1991 | Arnold |
| 5,011,469 A | 4/1991 | Buckberg et al. |
| 5,017,103 A | 5/1991 | Dahl |
| 5,040,944 A | 8/1991 | Cook |
| 5,097,849 A | 3/1992 | Kensey et al. |
| 5,108,411 A | 4/1992 | Mckenzle |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,147,186 A | 9/1992 | Buckholtz |
| 5,158,279 A | 10/1992 | Laffey et al. |
| 5,163,431 A | 11/1992 | Griep |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte et al. |
| 5,250,059 A | 10/1993 | Andreas et al. |
| 5,275,580 A | 1/1994 | Yamazaki |
| 5,357,963 A | 10/1994 | Mayol et al. |
| 5,373,619 A | 12/1994 | Fleischhacker et al. |
| 5,376,114 A | 12/1994 | Jarvik |
| 5,405,383 A | 4/1995 | Barr |
| 5,421,338 A | 6/1995 | Crowley et al. |
| 5,480,392 A | 1/1996 | Mous |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano et al. |
| 5,820,571 A | 10/1998 | Erades et al. |
| 5,827,171 A | 10/1998 | Dobak et al. |
| 5,851,174 A | 12/1998 | Jarvik et al. |
| 5,863,179 A | 1/1999 | Westphal et al. |
| 5,882,329 A | 3/1999 | Patterson et al. |
| 5,888,241 A | 3/1999 | Jarvik |
| 5,897,299 A | 4/1999 | Fukunaga |
| 5,938,672 A | 8/1999 | Nash |
| 5,954,745 A | 9/1999 | Gertler et al. |
| 6,001,078 A | 12/1999 | Reekers |
| 6,030,397 A | 2/2000 | Monetti et al. |
| 6,054,788 A | 4/2000 | Dombrovski et al. |
| 6,083,260 A | 7/2000 | Aboul-hosn |
| 6,123,725 A | 9/2000 | Aboul-hosn |
| 6,129,704 A | 10/2000 | Forman et al. |
| 6,135,729 A | 10/2000 | Aber |
| 6,152,693 A | 11/2000 | Olsen et al. |
| 6,168,624 B1 | 1/2001 | Sudai |
| 6,183,220 B1 | 2/2001 | Ohara et al. |
| 6,245,007 B1 | 6/2001 | Bedingham et al. |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,413,222 B1 | 7/2002 | Pantages et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,517,528 B1 | 2/2003 | Pantages et al. |
| 6,527,521 B2 | 3/2003 | Noda |
| 6,533,716 B1 * | 3/2003 | Schmitz-Rode ...... A61M 60/13 600/16 |
| 6,537,030 B1 | 3/2003 | Garrison |
| 6,537,247 B2 | 3/2003 | Shannon |
| 6,537,315 B2 | 3/2003 | Yamazaki et al. |
| 6,544,216 B1 | 4/2003 | Sammler et al. |
| 6,592,612 B1 | 7/2003 | Samson et al. |
| 6,652,548 B2 | 11/2003 | Evans et al. |
| 6,719,791 B1 | 4/2004 | Nuesser et al. |
| 6,841,910 B2 | 1/2005 | Gery |
| 6,858,001 B1 | 2/2005 | Aboul-hosn |
| 6,860,713 B2 | 3/2005 | Hoover |
| 6,945,977 B2 | 9/2005 | Demarais et al. |
| 6,974,436 B1 | 12/2005 | Aboul-hosn et al. |
| 6,976,996 B1 | 12/2005 | Aboul-hosn |
| 6,981,942 B2 | 1/2006 | Khaw et al. |
| 7,022,100 B1 | 4/2006 | Aboul-hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | Mcbride et al. |
| 7,467,929 B2 | 12/2008 | Nuesser et al. |

(56) References Cited

U.S. PATENT DOCUMENTS

| | | |
|---|---|---|
| 7,646,376 B2 | 1/2010 | Blersch |
| 7,731,675 B2 | 6/2010 | Aboul-hosn et al. |
| 7,841,976 B2 | 11/2010 | Mcbride et al. |
| 7,878,967 B1 | 2/2011 | Khanal |
| 7,927,068 B2 | 4/2011 | Mcbride et al. |
| 7,934,909 B2 | 5/2011 | Nuesser et al. |
| 8,079,948 B2 | 12/2011 | Shifflette |
| 8,439,859 B2 | 5/2013 | Pfeffer et al. |
| 8,721,516 B2 | 5/2014 | Scheckel |
| 8,888,728 B2 | 11/2014 | Aboul-hosn et al. |
| 8,998,792 B2 | 4/2015 | Scheckel |
| 10,584,589 B2 | 3/2020 | Schumacher et al. |
| 2001/0000528 A1 | 4/2001 | Cho |
| 2002/0123661 A1 | 9/2002 | Verkerke et al. |
| 2002/0151799 A1 | 10/2002 | Pantages et al. |
| 2002/0183840 A1 | 12/2002 | Lapeyre et al. |
| 2003/0135086 A1 | 7/2003 | Khaw et al. |
| 2003/0135940 A1 | 7/2003 | Lev et al. |
| 2003/0208097 A1 | 11/2003 | Aboul-hosn et al. |
| 2003/0231959 A1 | 12/2003 | Snider |
| 2004/0022640 A1 | 2/2004 | Siess et al. |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0113502 A1 | 6/2004 | Li et al. |
| 2004/0193046 A1 | 9/2004 | Nash et al. |
| 2004/0215222 A1 | 10/2004 | Krivoruchko |
| 2004/0215228 A1 | 10/2004 | Simpson et al. |
| 2004/0260237 A1 | 12/2004 | Squadrito |
| 2005/0135942 A1 | 6/2005 | Wood et al. |
| 2005/0180854 A1 | 8/2005 | Grabau et al. |
| 2006/0008349 A1 | 1/2006 | Khaw |
| 2006/0062672 A1 | 3/2006 | Mcbride et al. |
| 2006/0100565 A1 | 5/2006 | Aboul-hosn |
| 2006/0195004 A1 | 8/2006 | Jarvik |
| 2006/0198736 A1 | 9/2006 | Rousseau |
| 2007/0093887 A1 | 4/2007 | Case et al. |
| 2007/0118072 A1 | 5/2007 | Nash |
| 2007/0213761 A1 | 9/2007 | Murphy et al. |
| 2008/0004571 A1 | 1/2008 | Voss |
| 2008/0103591 A1 | 5/2008 | Siess |
| 2008/0132747 A1 | 6/2008 | Shifflette |
| 2008/0132748 A1 | 6/2008 | Shifflette |
| 2008/0183136 A1 | 7/2008 | Lenker et al. |
| 2008/0262584 A1 | 10/2008 | Bottomley et al. |
| 2008/0306327 A1 | 12/2008 | Shifflette |
| 2009/0060743 A1 | 3/2009 | Mcbride et al. |
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0171137 A1 | 7/2009 | Farnan et al. |
| 2009/0218728 A1 | 9/2009 | Moyer |
| 2009/0227892 A1 | 9/2009 | Krombach et al. |
| 2010/0041939 A1 | 2/2010 | Siess |
| 2010/0210895 A1 | 8/2010 | Aboul-hosn et al. |
| 2010/0268017 A1 | 10/2010 | Siess |
| 2011/0004046 A1 | 1/2011 | Campbell et al. |
| 2011/0071338 A1 | 3/2011 | Mcbride et al. |
| 2011/0236210 A1 | 9/2011 | Mcbride et al. |
| 2011/0238172 A1 | 9/2011 | Akdis |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0066140 A1 | 3/2013 | Mcbride et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |
| 2015/0073202 A1 | 3/2015 | Aboul-hosn et al. |
| 2015/0211542 A1 | 7/2015 | Scheckel |

FOREIGN PATENT DOCUMENTS

| | | |
|---|---|---|
| CA | 2613175 A1 | 1/2007 |
| CA | 2632420 A1 | 6/2007 |
| CA | 2701809 A1 | 4/2009 |
| CA | 2701810 A1 | 4/2009 |
| CN | 101278127 A | 10/2008 |
| CN | 101448535 A | 6/2009 |
| CN | 201492732 U | 6/2010 |
| DE | 2113986 A1 | 9/1972 |
| DE | 4414903 A1 | 11/1995 |
| DE | 10155011 A1 | 5/2003 |
| DE | 102005039950 A1 | 3/2007 |
| DE | 102010011998 A1 | 9/2010 |
| DE | 10336902 C5 | 4/2019 |
| EP | 0166104 A1 | 1/1986 |
| EP | 0364293 A2 | 4/1990 |
| EP | 0445782 A1 | 9/1991 |
| EP | 0480102 A1 | 4/1992 |
| EP | 0560000 A2 | 9/1993 |
| EP | 0768091 A1 | 4/1997 |
| EP | 0768900 A1 | 4/1997 |
| EP | 0629412 B1 | 1/1998 |
| EP | 0884064 A2 | 12/1998 |
| EP | 0916359 A1 | 5/1999 |
| EP | 0951302 A2 | 10/1999 |
| EP | 1034808 A1 | 9/2000 |
| EP | 0914171 B1 | 10/2001 |
| EP | 1207934 A2 | 5/2002 |
| EP | 1114648 B1 | 9/2005 |
| EP | 1019117 B1 | 11/2006 |
| EP | 2047873 A1 | 4/2009 |
| EP | 2047872 B1 | 9/2010 |
| EP | 2343091 A1 | 7/2011 |
| FR | 2788223 A1 | 7/2000 |
| GB | 2239675 A | 7/1991 |
| JP | H04126158 A | 4/1992 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 9944651 A1 | 9/1999 |
| WO | 9958170 A1 | 11/1999 |
| WO | 2000019097 A1 | 4/2000 |
| WO | 0027446 A1 | 5/2000 |
| WO | 0043054 A2 | 7/2000 |
| WO | 2000043053 A1 | 7/2000 |
| WO | 2001007760 | 2/2001 |
| WO | 2001007787 | 2/2001 |
| WO | 2001083016 A2 | 11/2001 |

(56) References Cited

FOREIGN PATENT DOCUMENTS

| | | |
|---|---|---|
| WO | 2002022200 A1 | 3/2002 |
| WO | 2002043791 A1 | 6/2002 |
| WO | 2003057013 | 7/2003 |
| WO | 2003103745 A2 | 12/2003 |
| WO | 2005002646 A1 | 1/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008034068 A2 | 3/2008 |
| WO | 2008054699 A2 | 5/2008 |
| WO | 2008106103 A2 | 9/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2009073037 A1 | 6/2009 |
| WO | 2010063494 A1 | 6/2010 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

OTHER PUBLICATIONS

Brochure Impella Pumpsystem of Impella CardioSystems AG, "Turning Lives Around," Aug. 2003 (4 pages).
Buecker A et al., "Use of a Nonmetallic Guide Wire for Magnetic Resonance—Guided Coronary Artery Catheterization," Investigative Radiology, 39:11, pp. 656-660 (2004).
Chemistry and Technology of Polys for Polyurethanes, by Rapra Technology Limited, Apr. 11, 2018.
Compendium of Technical and Scientific Information for the Hemopump Temporary Cardiac Assist System, 1988 (15 pages).
Dekker, Andre, et al., "Efficacy of a New Intraaortic Propeller Pump vs the Intraaortic Balloon Pump," Chest Journal; Jun. 2003 (7 pages).
Fluid Machinery Mechanical Engineer, NPTEL, Dec. 31, 2009.
Frazier, O.H., et al., "First Human Use of the Hemopump, A Cather-Mounted Ventricular Assist Device," Ann Thorac Surg., Feb; 49(2): pp. 299-304 (1990).
How Polyurethane is made, www.madehoe.com, Apr. 11, 2018.
International Preliminary Report on Patentability for PCT/EP09/008858, dated Jun. 7, 2011 (5 pages).
JOMED Reitan Catheter Pump Brochure, www.jomed.com/rcp (undated) (6 pages).
Lueger, Lexikon der Technik, "Lexikon der Feinwerktechnik", vol. 13, Deutsche Verlags-Anstalt GmbH, Stuttgart, seite 551 (4 pages) (1968).
Polyurethane Nanoparticles, Natural Polyol via Miniemulsion Technique by Zanettis-Ramos, Apr. 11, 2018.
Reitan, Oyvind et al., "Hydrodynamic Properties of a New Percutaneous Intra-aortic Axial Flow Pump," ASAIO Journal; May-June; vol. 16; 6 pages (2000).
Rothman, Martin T, "The Reitan Catheter Pump: A New Versatile Approach for Hemodynamic Support," London Chest Hospital Barts & The Long NHS Trust, presented at TCT Conference, Oct. 24-26, 2006, (40 pages).
Schmitz-Rode, T et al., "Temporary Pulmonary Stent Placement as Emergency Treatment of Pulmonary Embolism," Journal of the American College of Cardiology, 48:4, pp. 812-816 (2006).
Schmitz-Rode, T et al., "An Expandable Percutaneous Catheter Pump for Left Ventricular Support," Journal of the American College of Cardiology, 45:11, pp. 1856-1861 (2005).
Siess, Thorsten, "Systemanalyse und Entwicklung intravasaler Rotationspumpen zur Herzunterstutzung," Helmholtz-Institut, Jun. 24, 1998 (105 pages) and partial English translation (39 pages).
Verma, R et al., "Evaluation of a Newly Developed Percutaneous Thrombectomy Basket Device in Sheep with Central Pulmonary Embolisms," Investigative Radioloqv, 41:10, oo.729-734 (2006).
Wampler, Richard, K., "In Vivo Evaluation of a Peripheral Vascular Access Axial Flow Blood Pump," ASAIO Trans., Jul-Sep;34(3): pp. 450-454 (1988).
International Search Report and Written Opinion for International Application No. PCT/EP2011/003440 dated Nov. 9, 2011 (14 pp).
International Search Report for International Application No. PCT/EP2009/008858 dated Feb. 16, 2010 (4 pp).

* cited by examiner (VARIANT A)

(VARIANT B)

First state, section 0

First state, section 1

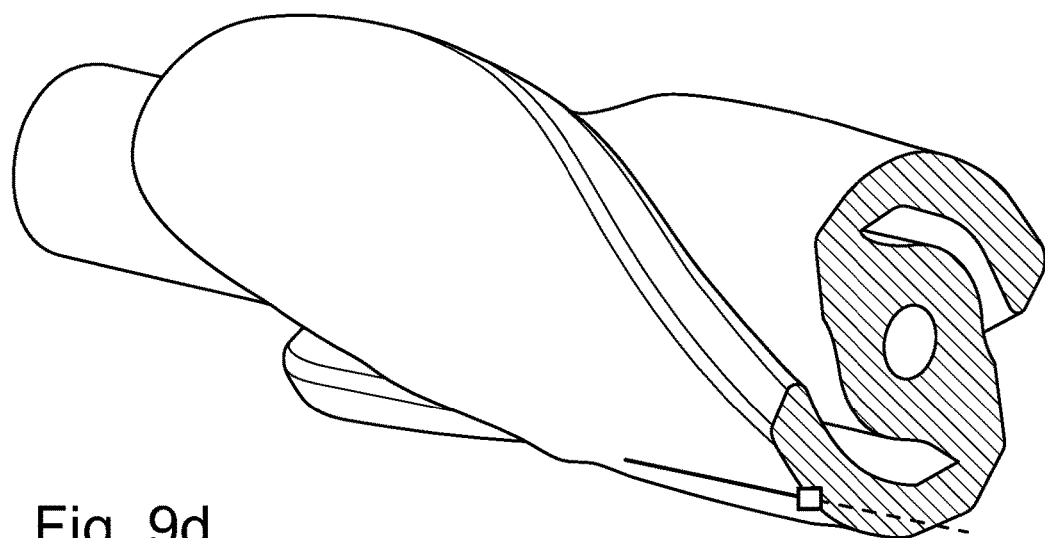
Fig. 9d
First state, section 2
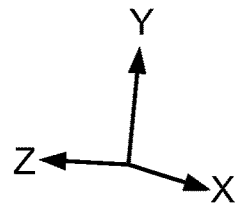
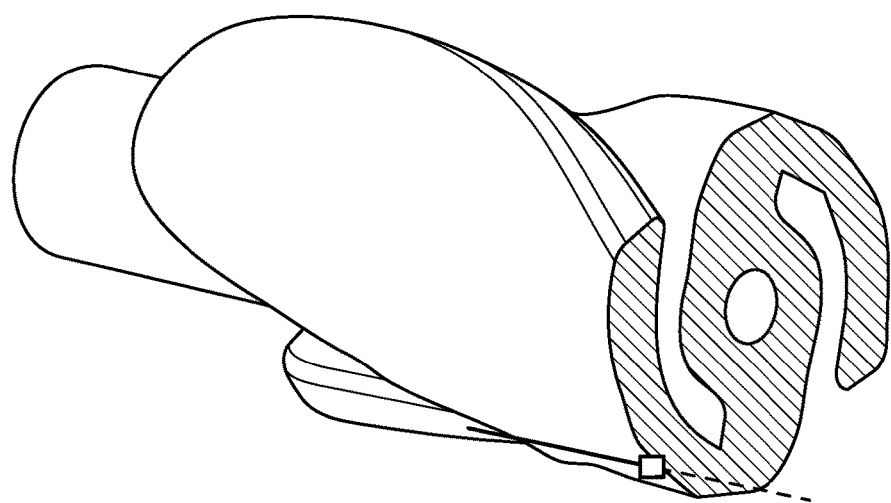
Fig. 9e
First state, section 3
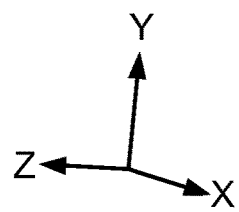

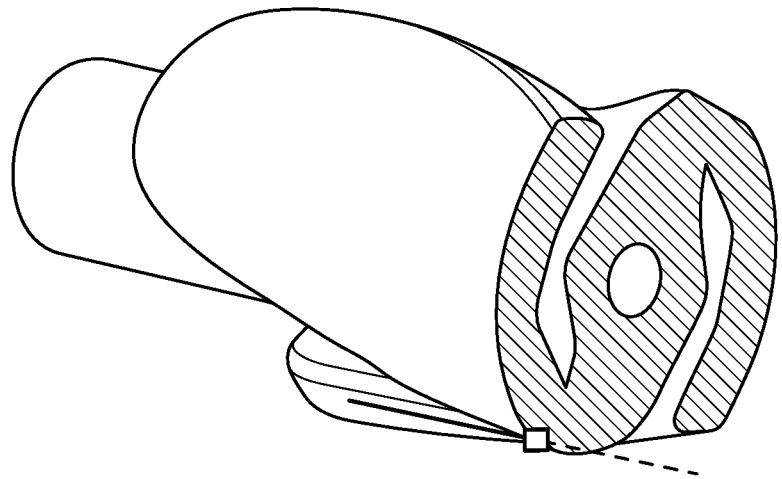
Fig. 9f
First state, section 4
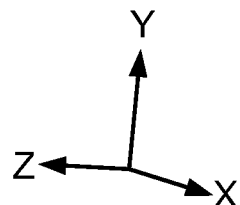
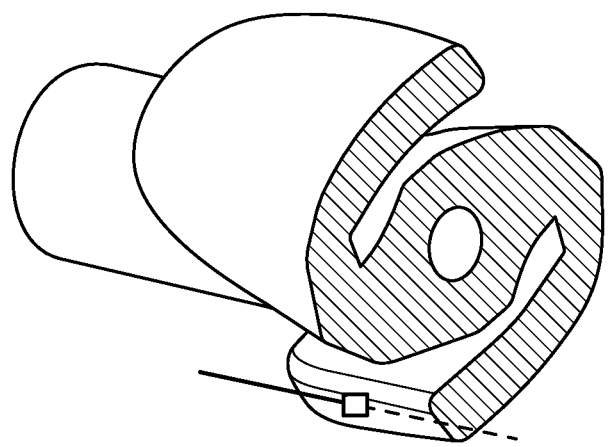
Fig. 9g
First state, section 5
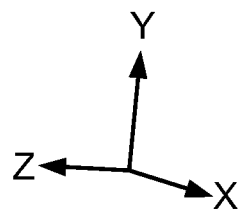

First state, section 6

ROTOR FOR A PUMP, PRODUCED WITH A FIRST ELASTIC MATERIAL

CROSS-REFERENCE TO RELATED APPLICATIONS

This application is a continuation of U.S. patent application Ser. No. 16/748,152, filed Jan. 21, 2020, now U.S. Pat. No. 11,313,228, which application is a continuation of U.S. patent application Ser. No. 15/671,326, filed Aug. 8, 2017 (now U.S. Pat. No. 10,584,589), which is a continuation of U.S. patent application Ser. No. 13/261,565, filed Mar. 21, 2013 (now U.S. Pat. No. 9,771,801), which entered the national stage on Mar. 21, 2013, and which is a United States National Stage filing under 35 U.S.C. § 371 of International Application No. PCT/EP2011/003440, filed Jul. 1, 2011, which claims the benefit of U.S. Provisional Patent Application No. 61/364,578, filed Jul. 15, 2010, and European Patent Application No. 10075303.7, filed Jul. 15, 2010, the contents of all of which are incorporated by reference herein in their entirety. International Application No. PCT/EP2011/003440 was published under PCT Article 21(2) in English.

BACKGROUND OF THE INVENTION

The invention resides in the field of mechanics and precision mechanics and relates to rotors for fluid pumps.

U.S. provisional application Ser. No. 61/364,559, U.S. provisional application Ser. No. 61/364,595, and U.S. provisional application Ser. No. 61/364,578 are hereby incorporated by reference.

Such pumps can be used in various ways in different spheres. In particular for use in surroundings which are difficult to access, it can be sensible to use compressible and expandable rotors in order to bring these in the compressed state to a place of use and to expand there in order to put be put into operation. Special applications are for example with pumps for circuitous pipe systems.

A further special application of such pumps takes place in the medical sphere. Pumps are used there in particular in the invasive field, i.e. introduced into the body of a patient. It is known to convey pumps in different forms, for example as catheter pumps, through natural body vessels, for example blood vessels, and to operate them there or for example also in a ventricle. For such special applications, a corresponding pump must have a particularly small construction, which concerns the radial diameter.

In order to design such pumps to be easily compressible and expandable, various measures are possible. Thus for example mechanisms have become known in order to design blades on corresponding pump rotors to be articulated and unfoldable and foldable radially. Rotors consisting also at least partially of so-called memory materials have become known, which change their shape as a function of the ambient temperature and are expandable or compressible in this way.

For example a compressible and expandable rotor (impeller) with a hub which carries various blades is known from US 2008/0114339 A1. Hub and blades can consist of the same material which has an elastic configuration so that the blades can be moved between a compressed position placed against the hub and an expanded, radially deployed position. High elasticity of the material is required for this purpose. For example particularly flexible polyurethanes are proposed there as material. Basically, also elastic polymers should be usable.

Basically, the rotor according to the mentioned document should be deformed between the compressed and the expanded form, on the one hand, in a linear range of the stress-strain curve and in addition in a non-linear range of the stress-strain curve in order to be able to perform the necessary large deformation travel.

BRIEF SUMMARY OF THE INVENTION

Against the background of the state of the art, the object underlying the present invention is to produce a rotor of the initially mentioned type which is compressible and expandable to a high degree and in the case of which, even with repeated compression and expansion, no permanent material changes take place.

The object is achieved according to the invention by the features of patent claim 1.

For this purpose, in the case of a rotor which can be actuated to rotate about an axis of rotation in order to convey a fluid and which drives the fluid in the axial or radial direction, it is provided that the rotor can be deformed reversibly elastically between a first, radially compressed state and a second, radially expanded state, as far as possible with minimised hysteresis or optimally entirely without hysteresis.

The second state is thereby a force-free state of the rotor, i.e. the position into which it falls back without the effect of external forces and which is extensively independent of whether this force-free state is achieved from the compressed or from an expanded third state.

At least one third state of the rotor is provided in addition, in which a pumping operation under fluid loading, i.e. by means of the fluid counterforces acting on the rotor, the rotor is further deformed, viewed from a first state, via the second state in the same direction. "At least" is therefore mentioned since, as a function of the speed of rotation, a plurality of such states can be provided. In particular, this third state can however occur at that speed of rotation at which the greatest pump power of the pump is achieved.

For this purpose, for example the rotor is formed and in particular the conveyor elements, preferably in the form of one or more conveyor blades, are formed such that the rotor or the conveyor elements is/are deformed during operation from the second state or more precisely the geometric shape of the second state during a rotation in the direction of rotation of a pumping operation in the direction of a third state. For this purpose, essentially the deformation of the rotor and/or of the conveyor elements, which has led from the first state to the second state, continues in the constant direction up to the third state. Advantageously, each conveyor element is thereby deployed further radially from the second state so that the fluid resistance during pumping operation is increased. Hence, an optimised compression/pump action is achieved in the case of a minimal wetted surface area of the rotor. The fluid resistance of the rotor is hence greater during rotation in the geometric shape of the third state than it would be during a rotation in the second state. In the case of a rotation during the pumping operation, for example the conveyor elements are pivoted/inclined in the second state relative to a hypothetical exactly radial orientation in the direction of the direction of rotation during the pumping operation. During the pumping operation they are then firstly deformed in the direction of a radial orientation, possibly also even further.

As a result, it can be ensured that the rotor does not touch the surrounding housing even with maximum radial orientation of the conveyor elements. The size ratios of housing and rotor can be adjusted to the maximum possible radial orientation and extension of the conveyor elements such that the pump gap between rotor and housing during operation with maximum deployment of the conveyor elements becomes optimal. As a result, the efficiency of the pump and/or its power and also its haemolytic properties are optimised. Provided that the conveyor elements cannot be deformed and/or pivoted beyond the state of maximum deployment and/or extension relative to the rotor, an optimised pump gap in operation can hence be ensured without the rotor touching the housing. In the case of pumps in which the conveyor elements are deformed by the fluid counter-pressure beyond a range of maximum orientation and are compressed again radially, this is not the case. During operation, such pumps have an enlarged pump gap unless it is accepted that the rotor grinds against the housing in specific states.

As a first approximation, a minimal but contact-free pump gap is hereby regarded as optimal, which pump gap promises the lowest flow losses and hence the best pump power with a prescribed operating diameter. If the gap width falls below a minimum value however, increased damage to the blood is to be expected, since then blood cells are squeezed in the pump gap and hence can be damaged.

In the sense of the present patent application, pump gaps between 0.01 mm and 1 mm, in particular between 0.01 mm and 0.3 mm, or very particularly between 0.03 mm and 0.1 mm, have proved to be right. These values relate to the expanded operating state of the pump in the human or animal body. The value ranges relate to a minimum spacing between the furthermost radially projecting point of the rotor and the corresponding point of the surrounding housing. The minimum spacing is hereby determined in purely radial direction (starting from the rotor axis). As "corresponding point of the surrounding housing" there is understood the point in the housing interior to which the corresponding point of the rotor could come closest during its rotation.

The corresponding values should be measured at the "design speed of rotation" of the pump, i.e. specific operating states. This is for example the speed of rotation at which the conveying power of the pump is maximal. A higher or lower design speed of rotation, which is necessary or sensible for specific therapies can however also be provided.

The rotor can in any case be designed thus within the scope of the embodiment of the present patent application such that the optimum extension/deployment of the conveyor elements is achieved at the highest sought operating speed of rotation at which normally (but not necessarily in every case) also the greatest pump power is to be expected. For this purpose, the conveyor elements can be deployed by pivoting relative to a rotor hub but also, if the individual conveyor elements are curved or folded in in the relaxed state, by extending the conveyor elements to the maximum in the radial direction. By means of suitable shaping and/or reinforcing of the conveyor elements, it is ensured that deformation beyond this state in practice does not take place or only to a negligible degree at an increased speed of rotation.

This represents an advantage relative to previously known pumps, the pump gap of which increases with increasing speed of rotation, as a result of which in such pumps the flow losses increase and an adequate power increase is no longer possible. It should be emphasised however that the above-indicated number values for the pump gap are intended to be valid for any type of pump, irrespective of whether and how the pump gap further reduces or not with increasing speed of rotation.

The present invention relates not only to a rotor but also to a pump having such a rotor and having a housing, the interior of which receives the rotor. The size of the interior is advantageously dimensioned such that the rotor does not touch the housing in the operating state, in particular if it concerns a compressible housing, after a radial expansion of the housing, and in fact neither during operation when the conveyor elements are extended fully radially nor when the pump is stopped and also in no intermediate state, for example during acceleration of the pump.

Advantageously, at least in at least an axial partial region in which also conveyor elements of the rotor are disposed, the interior of the housing is configured possibly also furthermore cylindrically with a constant diameter over the length or corresponding to the contour of the rotating rotor. This can be advantageous in particular when the rotor changes its length between the radially compressed state and the operating state, for example is lengthened in the radially compressed state.

The rotor can be configured such that it has a single or a plurality of blades which are circumferential helically on a hub and can be connected also in one piece to the hub and can consist of the same material as the hub. Also at least two blades which are circumferential helically can be disposed in the same axial region of the hub, overlapping axially entirely or partially and offset relative to each other on the circumference of the hub. Individual blades which are disposed axially one behind the other relative to the hub are also possible.

The rotor consists advantageously in one embodiment, at least partially of a first, elastic material in the form of a foam polyurethane, a solid polyurethane, a thermoplastic elastomer, a rubber or a superelastic material, in particular superelastic polymer.

Advantageously, the first material comprises a polyurethane based on a diisocyanate. The polyurethane can be produced advantageously with a polyether polyol, in particular a polyether polyol with 2 to 8 OH groups per molecule. Such polyether polyols can be produced from bivalent and multivalent alcohols and propylene- and/or ethylene oxide.

Basically an organically filled polyol, in particular a graft-, SAN- or polymer polyol or a PHD polyol can be used. These polyols can be used for increasing the elasticity of the first material.

Particularly advantageously, the first material can comprise a thermoplastic elastomer (TPE), in particular a polyamide TPE (TPA), a copolyester TPE (TPC), a styrene TPE (TPS), a urethane TPE (TPU), a rubber crosslinked with TPE (TPV) or an acrylonitrile/butadiene rubber+polyvinyl chloride (TPZ).

In particular there is possible as polyamide TPE (TPA), a thermoplastic polyamide elastomer, in the case of which the soft segments are configured with ether- and ester bonds, or a thermoplastic polyamide elastomer in which the first segments are configured as polyester (TPA-ES) or as polyether (TPA-ET).

In the case of the copolyester elastomers (TPC), the soft segments can likewise consist of ether- and ester bonds (TPC-EE) or of polyesters (TPC-EC) or of polyethers (TPC-ET). In addition, so-called olefin elastomers (TPO) and also elastomers with ethylene/propylene/diene+polypropylene (TPO-EPDM+PP) and those with ethylene/vinyl acetate+polyvinylidene chloride (TPO-EVAC+PVDC) are possible there.

Thermoplastic styrene elastomers can be configured as styrene/butadiene block copolymer (TPS-SBS), as styrene/isoprene block copolymer (TPS-SIS), as styrene/ethenebutene/styrene block copolymer (TPS-SEBS) or as styrene/ethenepropene/styrene block copolymer (TPS-SEPS).

Urethane elastomers (TPU) can comprise: aromatic hard segments and polyester soft segments (TPU-ARES) or aromatic hard segments and polyether soft segments (TPU-ARET) or aromatic hard segments and soft segments with ether- and ester bonds (TPU-AREE) or aromatic hard segments and polycarbonate soft segments (TPU-ARCE) or aromatic hard segments and polycaprolacton soft segments (TPU-ARCL) or aliphatic hard segments and polyester soft segments (TPU-ALES) or aliphatic hard segments and polyether soft segments (TPU-ALET).

For example, the materials "Carbothane®" (TPU) of the company Lubrizol, "Barex®" of the company IMEOS Barex, "ISOPLAST™" of Lubrizol Advanced Materials Inc. or "Biresin®" of the company Sika can concretely be used.

Thermoplastic elastomers with crosslinked rubber (TPV) can comprise highly crosslinked EPDM+BP (TPV-(EPDM-X+PP)) or be configured as highly crosslinked acrylonitrile/butadiene rubber+PP (TPV-(NBR-X+PP)) or as highly crosslinked natural rubber+PP (TPV-(NR-X+PP)) or as highly crosslinked epoxidated natural rubber+PP (TPV-(ENR-X+PP)) or as crosslinked polybutylacrylate+PP (TPV-(PBA-X+PP)).

The thermoplastic elastomers essentially have the rubber-elastic properties of crosslinked elastomers and combine these with the advantage of thermoplastic processability.

Basically, these can consist of a thermoplastic polymer matrix with crosslinked or uncrosslinked elastomer particles as soft phase (so-called polymer blends). However, they can also be configured as so-called graft- or copolymers which comprise, in one polymer molecule, thermoplastic sequences and elastomeric sequences which can be demixed locally so that the thermoplastic sequences form physical crosslinking points in the continuous matrix of the elastomeric sequences (example: styrene block copolymer (TPS)).

At the temperature of use, the elastomeric sequences are above their glass temperature, whilst the thermoplastic sequences are below their glass temperature (in the case of amorphous polymers) or the melting temperature (in the case of partially crystalline polymers).

Copolyamides (TPA)

For the production of copolyamides, lactam dihydroxypolytetrahydrofuran and dicarboxylic acid (TPA-ET) can be used, for the production of TPA-EE: laurinlactam, adipinic acid and bishydromethylcyclohexane.

Thermoplastic Elastomers with Copolyesters (TPC)

For the production of TPC (thermoplastic elastomers with copolyesters), soft segments made of polyalkylene ether diols and/or long-chain aliphatic dicarboxylic acid esters with partially crystalline PBT segments can be used. The corresponding materials are hydrolysis-resistant and temperature-resistant.

Polyolefin Elastomers (TPO)

Polyolefin elastomers (TPO) can be produced as blends on the basis of isotactic PP- and ethylene-propylene rubbers (EPDM).

The thermoplastic olefin elastomer TPO-(EVAC-PVDC) is produced on the basis of alloys with PVDC hard domains and a partially crosslinked soft EVAC-copolymer matrix.

Thermoplastic Elastomers with Polystyrene (TPS)

These can be configured for example as three-block copolymers TPS-SBS by being able to be constructed by anionic polymerisation, e.g. with lithium butyl, in succession blocks made of styrene and butadiene and optionally once again of styrene. Similarly, polymers of the type SIS (I=isoprene) can be produced (TPS-SIS). The polystyrene chain portions aggregate thereby to form the hard domains and the polybutadiene chain portions to form flexible rubber regions.

TPS can also be used in multicomponent injection moulding. Good adhesion is achieved for example with the following plastic materials: PE, PP, PS, ABS, PA, PPO, PBT (abbreviations cf. Saechtling, Kunststofftaschenbuch, 29th edition 2004, Verlag Hansa, Munich/Vienna).

Such materials can then be combined in the injection moulding with the first material, for example as reinforcing structures.

Polyurethane Elastomers (TPU)

TPU can be produced as block copolymers by polyaddition of long-chain diols (chain lengthener: 1,4-butanediol or 1,6-hexanediol, long-chain diols: polyether diols, polyester diols, polycarbonate diols) with aliphatic diisocyanates. These are materials which are distinguished by high resistance to wear and tear and flexibility and also chemical resistance and high bio-compatibility.

TPV, Polyolefin Blends with Crosslinked Rubber

These materials have crosslinked rubber soft segments and consequently are very elastic.

Further Thermoplastic Elastomers

There are possible as further thermoplastic elastomers, those based on PVC with NBR or PBA (NBR[TPZ-(NBR+PVC)] or PBA[TPZ-(PBA+PVC)]).

A further advantageous embodiment of the invention provides that the first material is configured as natural or synthetic rubber, in particular as R-rubber, as M-rubber, as O-rubber, as Q-rubber, as T-rubber or as U-rubber.

Corresponding rubbers can advantageously be used also with softeners and extended with oil.

The Individual Rubber Variants:

R-Rubbers

Natural rubber (NR) has high strength and elasticity. It is temperature-stable and elastic with low mechanical damping.

Advantageously, also isoprene rubber (IR) with often even higher elasticity can be used.

Also the use of butadiene rubber (BR) is possible. For example also a carboxyl group-containing butadiene rubber can be used here.

Advantageously, also a chloroprene rubber (CR) can be used, in particular also a styrene-chloroprene rubber.

Also the use of styrene-butadiene rubber (SBR) can be advantageous. For example a carboxyl group-containing styrene-butadiene rubber can be used here.

Also the use of nitrile-butadiene rubber (NBR), nitrile-chloroprene rubber (NCR) and butyl rubber (IIR, CIIR, BIIR) with IIR as copolymer is conceivable. In addition, also an isoprene-styrene rubber (SIR) or a polynorbonene rubber (PNR) can be used. Also the use of trans-polyoctenamer rubber (TOR) or hydrated NBR-rubber (HNBR) is conceivable.

M-Rubbers

There can be used amongst the M-rubbers, for example ethylenepropylene(diene) rubbers (EPM, EPDM). EPM can thereby be crosslinked with peroxides, EPDM also vulcanised with sulphur.

There can also be used ethylene-acrylic ester rubbers (AECM), ethylene-vinylacetate rubbers (EAM), chlorosulphonated PE-rubber (CSM), chlorinated PE-rubber (CM), acrylate rubber (ACM (AEM, ANM)), fluorine rubber (FKM), propylenetetrafluoroethylene rubber (FPM) or perfluorene rubber (FFKM).

O-Rubbers

There are conceivable as O-rubbers, bichlorohydrine homopolymer-, copolymer- and terpolymer rubbers (CO, ECO, ETER). Epichlorohydrine elastomers can be crosslinked with amines. Vinyl group-containing terpolymers can also be vulcanised with sulphur or peroxide.

Also the use of a propylene oxide rubber (PO) is conceivable.

Q-Rubbers

There can be used as silicone rubbers (Q-rubbers), polydimethylsiloxane rubber (MQ), methylphenylsiloxane rubber (MPQ), methylvinylsiloxane rubber (VMQ), methylphenylvinylsiloxane rubber (PVMQ), methylfluorosiloxane rubber (MFQ) and also fluorosilicone rubber (MVFQ) and liquid silicone rubber (LSR). Silicone rubbers have chains with siloxane groups and are physiologically safe. They have high permanent elasticity.

T-Rubbers

There can be used as T-rubbers with sulphur, polysulphide rubbers (TM, ET) and also thiocarbonyldifluoride copolymer rubber (TCF).

U-Rubbers

There can be used as U-rubbers, nitrose rubber (AFMU), urethane rubber and also polyester/polyether rubber (EU, AU). The processing of urethane rubber can be produced, in the case of thermoplastic PUR elastomers, by thermoplastic shaping or generally by casting of a reactive mixture or the production of a prepolymer and mixing in of fillers and crosslinking agents with subsequent vulcanisation in heated moulds. AU and EU have exceptionally high strength, flexibility and elasticity. They combine this property with a high resistance to wear and tear. AU thereby has better water resistance than EU.

There can be used in addition, polyphosphazenes (PNF, FZ, PZ) with alternating chains with phosphorus and nitrogen, for example fluorophosphazene rubber. In addition, the use of phosphazene rubber with fluoroalkyl or fluorooxyalkyl groups and also phosphazene rubber with phenoxy groups is conceivable. Also the use of polyperfluorotrimethyltriazine rubber (PFMT) is conceivable.

The first material can advantageously comprise at least one additive which reinforces it mechanically.

The additive can also be configured or introduced into the material such that it makes the latter mechanically anisotropic. This can be achieved for example by insertion of fibres, gratings or nets or as a result of an anisotropic interaction of the additive with the remaining components of the first material taking place. The first material can also be provided, by the production method of the rotor, with anisotropic mechanical properties, for example by means of anisotropic crosslinking processes or by the use of anisotropic casting, injection moulding or extrusion or drawing methods.

Corresponding reinforcing fibres can be configured for example as glass fibres, carbon fibres, plastic material fibres or natural fibres. These can be orientated for example in common in a preferential direction or be disposed at least parallel to each other.

Glass fibres can be used for example in a length of a few micrometres to millimetres.

There can be used as fibres, also organic materials, such as wood dust, cellulose, cotton fibres, cotton cloth cuttings or silk strands. In addition, artificial silk strands, mineral fibres, short- and long glass fibres and also glass mats can be jointly processed during processing by pressing, injection pressing and injection moulding.

There can be used as carbon fibres, carbonised and graphitised CF-reinforcing fibres from the polyacrylonitrile fibre. Also carbon spun fibres can be used which are available as monofilaments and uni- or multiaxial textile structures. The smooth fibre surfaces can thereby be roughened by an oxidising treatment.

PPTA, PAI or PBI are possible as high-temperature plastic material fibres. These are spun from specific solvents, such as for example NMP=N-methylpyrolidone. PPTA reinforcing fibres are spun to be highly crystalline from liquid crystal solutions.

The described fibres, fabrics and additives can be combined advantageously with the various above-mentioned volume materials, such as polyurethanes, thermoplastic elastomers and rubbers.

The above-mentioned materials are suitable, because of their intrinsic stability, in particular for the rotor to achieve the second state without the effect of external forces.

This is particularly advantageous in cases in which the rotor is intended to be introduced into a human vessel in the compressed first state and subsequently, before the beginning of the rotation, is intended independently to adopt a specific expanded position from which the rotation of the rotor then begins.

It is hereby provided preferably that the rotor which is initially actuated to rotate in the second state adopts a third state under fluid loading. It is hereby advantageous that the third state can be defined precisely depending upon coordination of the material, in practice as in the case of a "baseball glove" which is compressible in one direction and has a defined "end position" in the other direction in order to ensure the best possible function. This presently has the great advantage that a specific operating position (third state) of the rotor can be ensured also independently of the speed of rotation, which can be important for technical flow adaptation/design. This is designed preferably such that the radial deflection (measured from the centre of the axis of the rotor to the radially outermost point) of a rotor blade in the speed of rotation range of 5,000 rpm to 40,000 rpm essentially remains the same, preferably that $\varepsilon_{2 \to 3} < 0.05$, particularly preferably $\varepsilon_{2 \to 3} < 0.03$, $\varepsilon_{2 \to 3}$ being defined as $$\varepsilon_{2 \to 3} = \frac{|r_2 - r_3|}{r_2},$$

wherein $r_2$=maximum radial extension in the second state measured from the rotor centre to the radially outermost point;

$r_3$=maximum radial extension in the third state measured from the rotor centre to the radially outermost point.

A further advantageous development provides that the rotor is configured such that, during standstill, it returns from the third state reversibly elastically into the second state. This means that this movement belongs in fact to "Hooke's straight line". The coordination of the material is hereby simpler than in the case of objects according to the state of the art, preferably it concerns a homogeneous plastic material rotor or a plastic material rotor in which metallic inclusions (or inclusions made of another material) are provided. The primary deformability is hereby effected not by weakened portions in the foot region of the rotor blades (i.e. close to the hub) but essentially over the entire rotor (regarding the radial length). This again makes it readily possible to reinforce the hub region with metallic inclusions/ struts, also in order to ensure a defined flow shape during operation, even at high speeds of rotation, for example in the range of 5,000 rpm to 40,000 rpm.

A further advantageous development provides that the rotor is configured such that adoption of the first state from the second state and adoption of the third state from the second state are effected in opposite directions. This means (see also diagrams which are referred to further on) that the first state is effected in the first quadrant of a stress-strain diagram (stress=ordinate, strain=abscissa) and the third state is provided in the third quadrant.

This embodiment had considerable advantages since as a result an "end stop" (whether due to material properties or mechanical blocking as a result of embedded elements) can be effected, on the one hand, for the third state in order to provide the same operating point over a speed of rotation band. On the other hand, this has the advantage that, during commissioning of the rotor, in particular in the case of intraventricular applications in which access by medical personnel directly is limited, for example into the ventricle of a heart, "automatic" deployment by the fluid pressure is effected. This has a crucial advantage relative to devices in which the first state and the third state both take place in the first quadrant. In the case of such devices, the deployment force (for the deployment of the first into the second state, i.e. the unmoved state) would in fact require to be chosen to be strong such that secure deployment is possible even against an applied fluid pressure. In particular in time-critical situations in the case of resuscitation of a patient, this can be a crucial disadvantage.

Therefore, it is required according to the invention, in a preferred embodiment, that the self-determined deployment of the rotor from a compressed first state into the expanded second state is possible within at most ten seconds during withdrawal from the sheath and a further deformation into the third state can then be effected immediately. This is also more favourable with respect to force than in the case of the above-mentioned alternative in which the first state and third state are both in the first quadrant since creep processes and hystereses are significantly better in the case of the variant according to the invention.

A further advantageous development provides that the rotor is configured such that, starting from the initial second state during transfer into the first state, subsequently into the third state and finally back into the second state, it has a permanent residual strain EH of preferably less than 8%, particularly preferably less than 3%, very particularly preferred less than 1%. .εH is defined here as $$\varepsilon_H = \frac{|r_4 - r_0|}{r_0},$$

wherein $r_4$=maximum radial extension in the second state (up to the end point, i.e. at the end, see FIG. 11), measured from the rotor centre to the radially outermost point (measuring mode see FIG. 6);

$r_0$=maximum radial extension in the second state (at the initial time see FIG. 11), measured from the rotor centre to the radially outermost point (measuring mode see FIG. 6).

It is hereby assumed that the first state lasts for 0 hours to 12 hours and the third state lasts for 0 hours to 2,000 hours and the temperature is always between 1° C. and 50° C., preferably between 18° C. and 40° C.

A further advantageous development provides that the rotor has at least one rotor blade, the rotor blade having a pressure side and a suction side and the pressure side having a concave cross-section or at most a turning point. The pressure side is hereby the side which operates counter to the fluid pressure, for example of the blood in the ventricle. Preferably, the geometry of the rotor blade concerns a rotor blade, the flow pressure side of which in all cross-sections perpendicular or parallel to the axis of rotation is concave, is straight or at most has a turning point. As a result, high efficiency of the rotor results; stringing-together of convex and concave cross-sections, which is problematic with respect to unfavourable geometry and technical production, is hence not required.

The present invention relates in addition to an intraventricular blood pump, comprising a rotor according to one of the preceding examples and also a sheath for compressing the rotor. Compression of the rotor is hereby effected by penetration of the rotor into the sheath, preferably by penetration of the pump head with the rotor situated therein into the sheath, particularly preferably by pulling the pump head with the rotor into the sheath. Both sheath and rotor can hereby consist of the above-mentioned plastic materials.

In order to avoid adhesion processes, creep processes and also hystereses, it has proved advantageous that rotor and sheath are provided initially unjoined. This means that the rotor, for example upon delivery from the manufacturer to a hospital, is not compressed in the sheath. This makes it possible that, immediately before the implantation, the rotor is tested firstly, for example in a test apparatus, and the medical personnel (this is also important possibly for reasons of liability) hence test the rotor and then introduce or insert it themselves into the sheath. After unfolding the rotor in the human body, for example in a ventricle, the latter is then set in operation. It is hereby advantageous that no settling and/or adhering results; an operational check is possible and hystereses are reduced. Preferably, handling of the equipment is such that, during the implantation of the rotor, the rotor is stored for at most ten hours in the compressed first state, preferably less than three hours, very particularly preferred less than 30 minutes.

BRIEF DESCRIPTION OF THE DRAWINGS

In the following, the invention is shown in a drawing and described subsequently with reference to an embodiment.

There are thereby shown

FIGS. 9b-9h sections at different axial positions along the rotor axis corresponding to FIG. 9a, FIG. 10 a view of the rotor shown in FIGS. 9a-9h in the state A2, FIGS. 11/12 hysteresis curves, FIGS. 13/14 illustrations of the blade lengthening between radially compressed and expanded state, and also FIG. 15 illustration of the variable gradient of a rotor in an operating state.

DETAILED DESCRIPTION OF THE INVENTION

Figure 1:
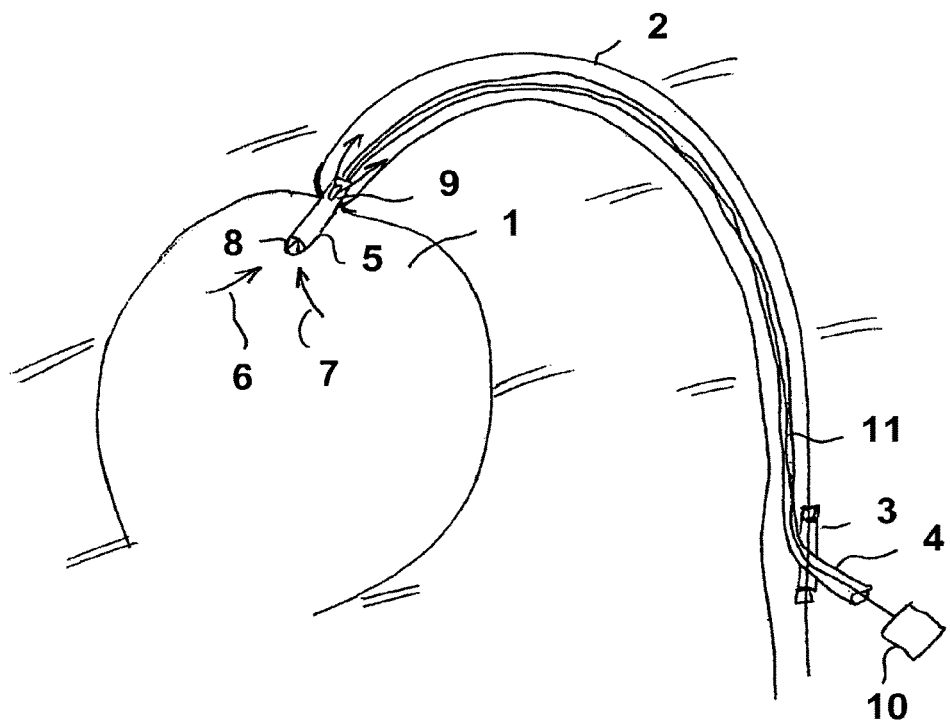
FIG. 1 schematically, the arrangement of a heart catheter pump in a ventricle.

FIG. 1 shows, in a simplified schematic illustration, a ventricle 1 of a heart chamber into which a blood vessel 2 (aorta) opens. In the region of the heart valve, a pump 5 is inserted at least partially from the blood vessel 2 into the ventricle 1. The pump 5 is moved forward through a hollow catheter 4 by means of a sheath 3 into the inside of the body of a patient and through the blood vessel 2 into the ventricle. Within the hollow catheter 4, a drive shaft 11 extends, which can be actuated by means of a motor 10 provided outside the body and which itself drives the rotor of the pump 5.

The pump 5 has a suction cage 8 on its front, distal side, through which, symbolised by the arrows 6, 7, blood is suctioned in. This is expelled through openings 9 at the proximal end of the pump or a discharge hose into the blood vessel 2. By means of the conveying function of the pump 5, this assists the heart pump activity or replaces it partially.

In order that the pump 5 is expandable radially inside the ventricle 1 after transport through the blood vessel 2, both the rotor and the pump housing or the discharge hose are radially compressible and expandable in the illustrated example.

Figure 2:
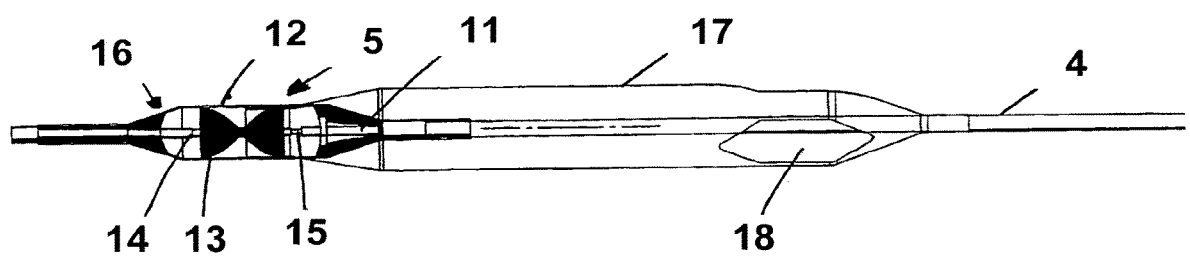
FIG. 2 a heart catheter pump in an enlarged illustration.

These are illustrated in more detail in FIG. 2. Inside a pump housing 12 which can have an expandable mesh braiding and be covered by a dense membrane, a rotor 13 which has a screw-shaped blade and a hub is disposed. The hub can be mounted in bearings at its proximal end 15 and also the distal end 14.

A suction cage 16 is disposed at the distal end of the housing 12. Blood is suctioned in through this. A so-called pigtail 19 which forms a spacer as a flexible continuation is disposed at the distal end of the pump 5 in order to prevent, in the suction operation or during transport, impact against heart walls or vascular walls or being suctioned against inner surfaces and in order to stabilise the position of the pump.

The hub 14, 15 is connected to the flexible actuatable shaft 11 at the proximal end of the pump.

A discharge hose 17 is drawn over the housing 12 of the pump, into which discharge hose the pump 5 pumps the blood and through which it can flow past the heart valve into the aorta or the blood vessel 2. It is expelled there through discharge openings 18 out of the discharge hose into the blood vessel.

Figure 3:
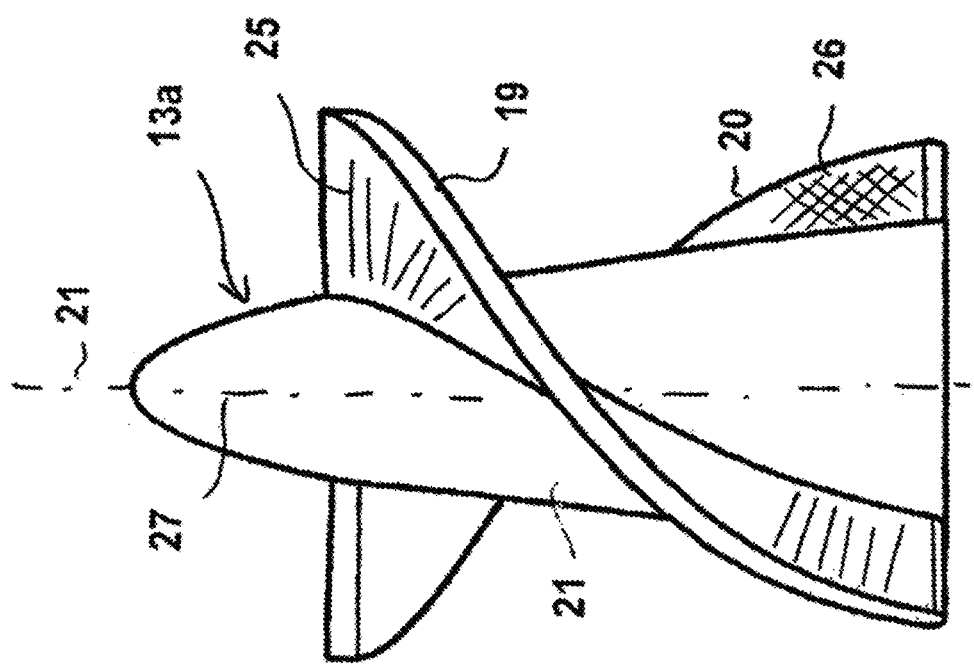
FIG. 3 a rotor of a pump in three-dimensional view with a hub.

The rotor 13 is illustrated in more detail in FIG. 3. It has a hub 13a made of a thermoplastic elastomer to which two blades 19, 20, which are wound into each other in the manner of a screw, are connected in one piece. These are illustrated in the expanded state which they adopt during operation under the effect of force of the fluid counter-pressure. The blades can be folded in almost completely against the hub 13a in the compressed first state. The material elasticity of the blades and also of the hub is sufficient for this purpose and the material is produced such that the corresponding deformation is reversible. The deformation travel and the force-free, relaxed position are advantageously dimensioned such that the material can stretch as far as possible over the total travel along a hysteresis-free stress curve.

The rotor is hence designed such that the occurring shear, tensile or pressure deformations take place inside the proportional range of Hooke's straight line. This can be achieved by suitable design and a correspondingly chosen operating point of the deformation.

In FIG. 3, reinforcing fibres 25, which extend approximately radially, viewed from the axis of rotation of the hub 13a, and reinforce the blades 19, 20, are indicated.

In addition to the radially extending reinforcing fibres, reinforcing fibres which extend at right angles hereto can also be provided, which reinforcing fibres can also be woven with the first reinforcing fibres to form a flat woven material.

Also reinforcing fibres 26 which are configured as woven material made of two groups of fibres extending perpendicularly to each other are illustrated by way of example on the blade 20, all the fibres extending at an angle of for example 45° relative to the axis of rotation 27.

The reinforcing fibres 25, 26, can be configured for example as glass fibres or as polyamide fibres or carbon fibres. They are mixed in during production of the rotor either with the injection moulding material during the extrusion, in particular if short fibres are involved which need not necessarily be orientated or they are inserted into an injection moulding—or casting mould and extrusion-coated by means of a material. This material can be for example a polyurethane, a thermoplastic elastomer or a rubber.

Figure 4:
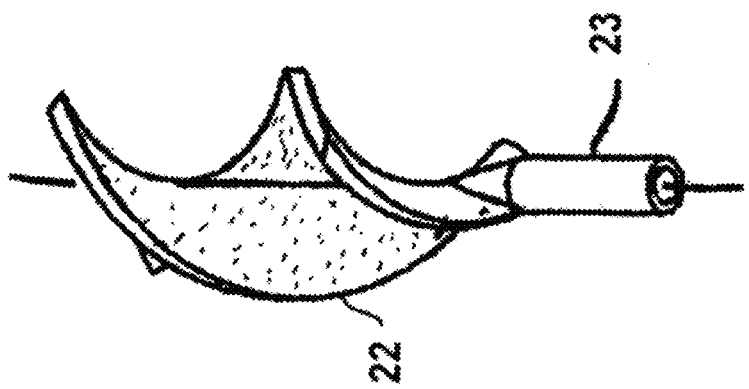
FIG. 4 a hub-free rotor in a three-dimensional view.

In FIG. 4 a hub-free rotor is represented, in the case of which a single blade 22 is connected to a shaft end 23 and can be actuated by this. The blade 22 can be reinforced for example by nanoparticles which are embedded in the first material and then form a component of the first material. As illustrated with reference to FIG. 3, a hub-free rotor can also be reinforced with corresponding fibres.

Figure 5:
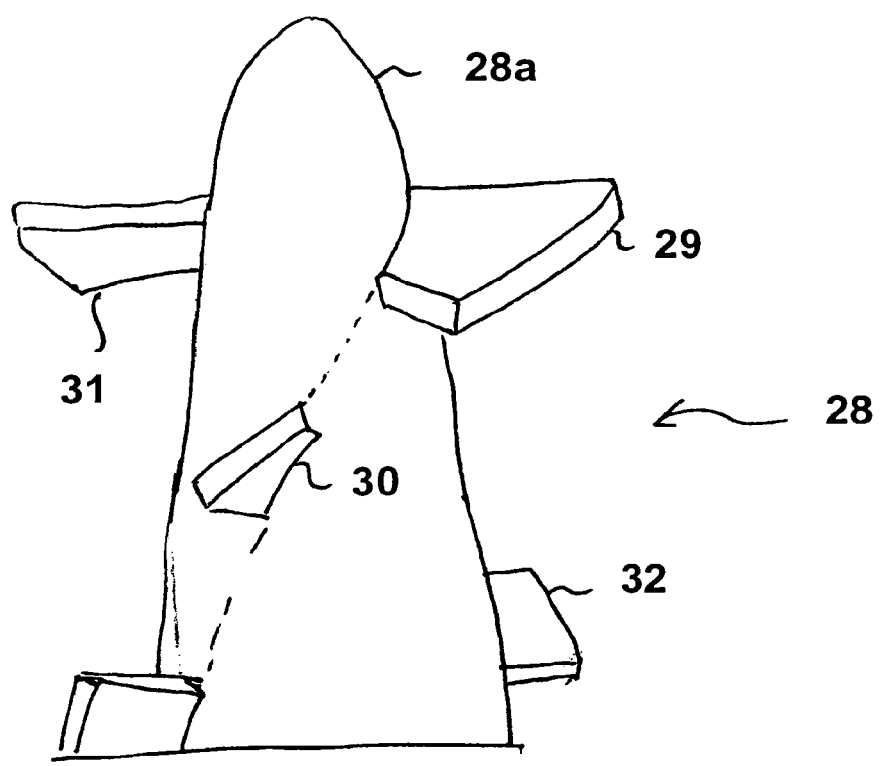
FIG. 5 in a three-dimensional view, a rotor having a plurality of blades.

FIG. 5 shows a rotor 28 with conveyer blades 29, 30, 31, 32 which are all disposed and secured individually on the hub 28a. Such a separate arrangement of conveyer blades on the hub effects simpler foldability on the hub and hence simpler compression of the rotor.

The individual blades 29, 30, 31, 32 can consist respectively of the same elastomeric material and also be connected in one piece to the hub. They can be reinforced by means of a pulverulent, granulate or fibrous additive up to the desired rigidity.

All the explanations in the present applications with respect to the angle α and β (see in particular patent claim 16 as originally filed and associated description) and also the "unwinding" or "gradient" of the blades are valid also for blade arrangements which, as for example in FIG. 5 are configured as a series of a plurality of blades which are disposed one behind the other. With respect to the lengthening, it is valid that, in the case of a plurality of blades which are situated axially one behind the other, the change in the overall length between the most proximal point of the proximal blade and the most distal point of the distal blade is measured.

The material of the hub 28a can also be reinforced by inserting reinforcing fibres or other additives.

Figure 6:
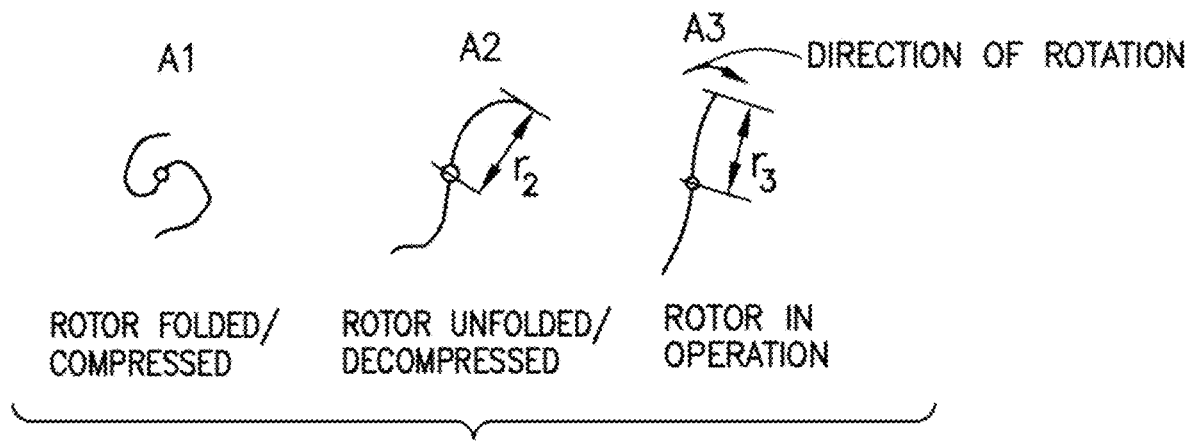
FIG. 6 a schematic view of rotor deformation states according to variant A.
Figure 7:
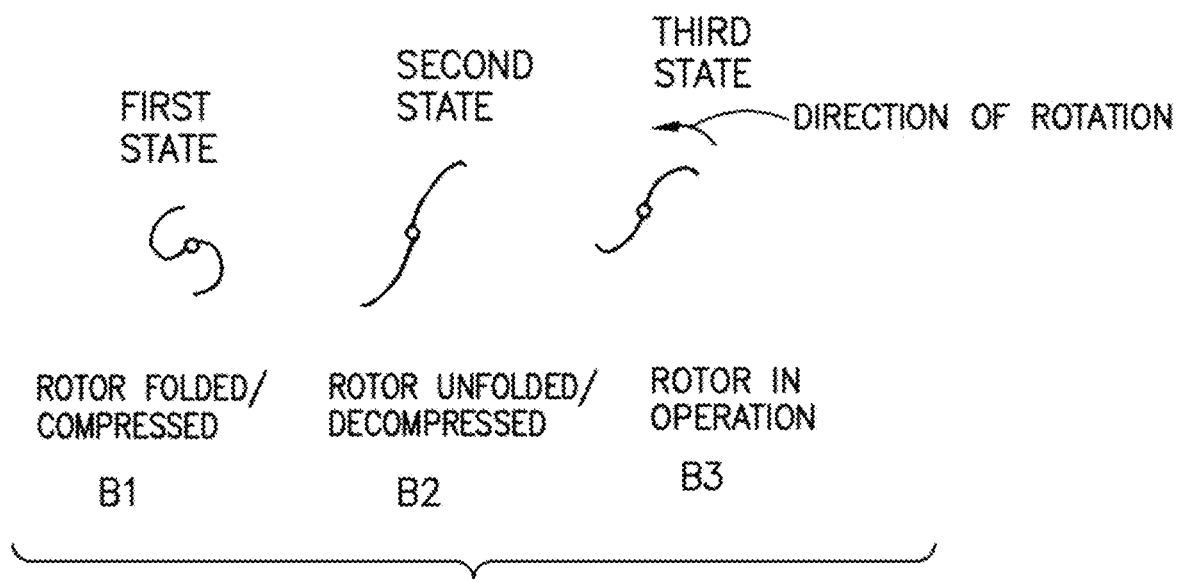
FIG. 7 a schematic view of rotor deformation states according to variant B.

FIG. 6 shows schematically a preferred embodiment of the invention with respect to the deformation states of the rotor. Respectively single-blade rotors (i.e. rotors in which one rotor blade protrudes on both sides of the axis) are hereby shown. In FIGS. 6 and 7, a plan view on the axis (the axis protrudes out of the paper plane) is hereby shown; the axis is hereby characterised by a small circle.

In FIG. 6 (subsequently also termed variant A), the folded/compressed initial position of the rotor (also termed A1) is shown. This is for example the initial position of the rotor (first state) in which it is inserted into a sheath.

The second state (state A2) shows the unfolded/decompressed rotor which is still unloaded by fluid pressure. This state occurs for example if an intraventricular blood pump has been removed from the sheath after introduction into the human heart.

The third state (A3) is the state in which the rotor moves. A rotation of the rotor in clockwork direction is hereby effected in FIG. 6. It is clear that, as a result, even greater deformation is effected in the "unfolded" state, a quasi "self-stabilisation" of the rotor is effected. Hence the operating point can be adjusted exactly, for example by a limit stop and/or by corresponding design of the material.

The initial state is in turn B1, state B2 is produced after the unfolding, Conveyance of fluid is effected however here in anticlockwise direction so that rather the rotor is folded in radially again. This means that the unfolding force between states B1 and B2 must be so great that the fluid conveying operation does not cause the rotor to collapse such that the latter can no long operate properly.

Figure 8:
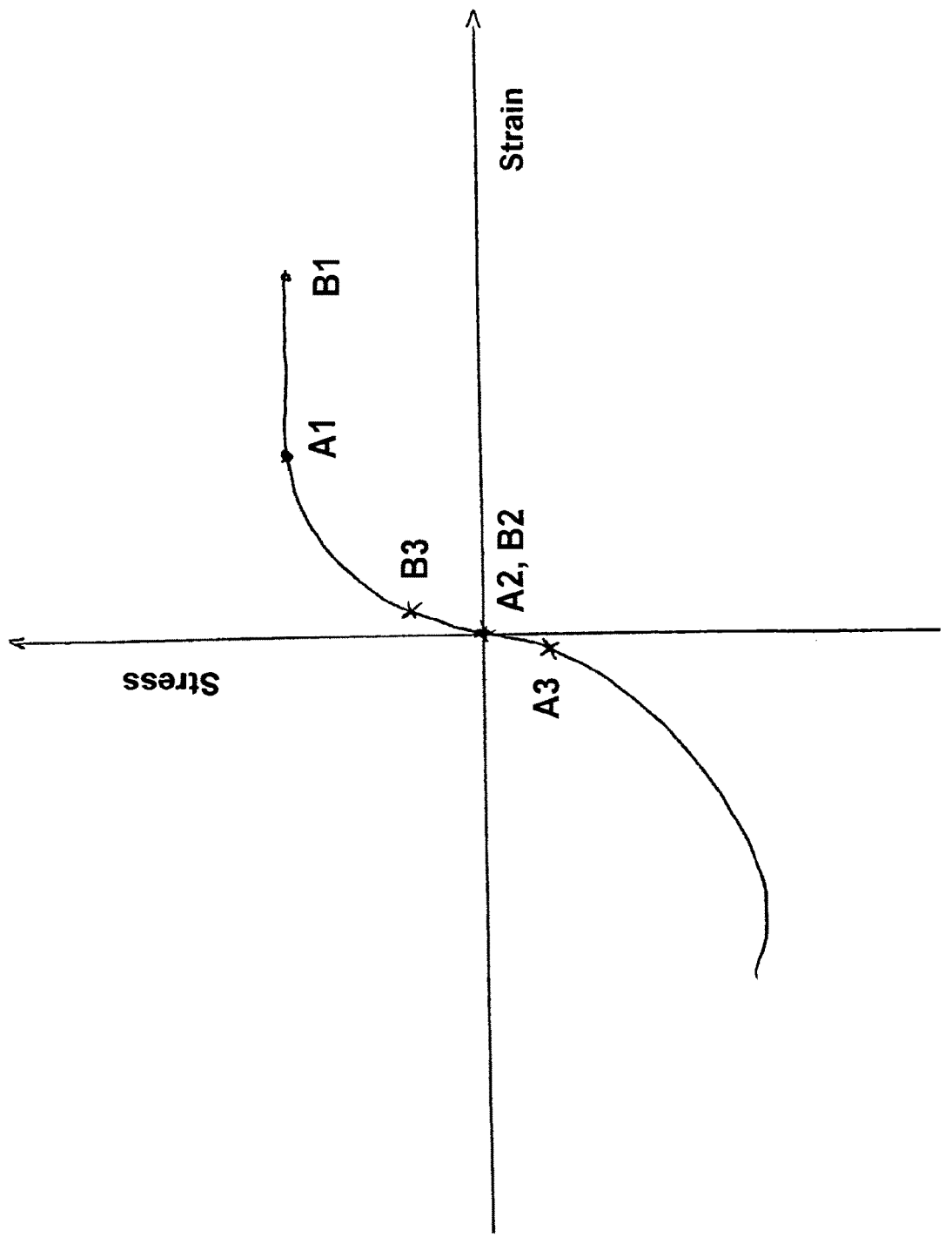
FIG. 8 a stress-strain diagram for the states shown in FIGS. 6 and 7.

These geometric ratios are clarified once again in FIG. 8. In the illustrated diagram, the strain is shown on the abscissa and the stress on the ordinate. A1 or B1 is shown here in the first quadrant. Upon removing the rotor from the sheath, the force-less states A2 or B2 result. During the conveying operation, deformation to A3 or B3 is then produced. It must hereby be emphasised that A3 is in the third quadrant, whereas B3 is in turn in the first quadrant. This means that, in the preferred embodiment of the invention, A1 and A3 respectively stand in diagonal quadrants, whilst B1 and B3 (in the less preferred variant) are disposed in the same quadrant.

Figure 9A:
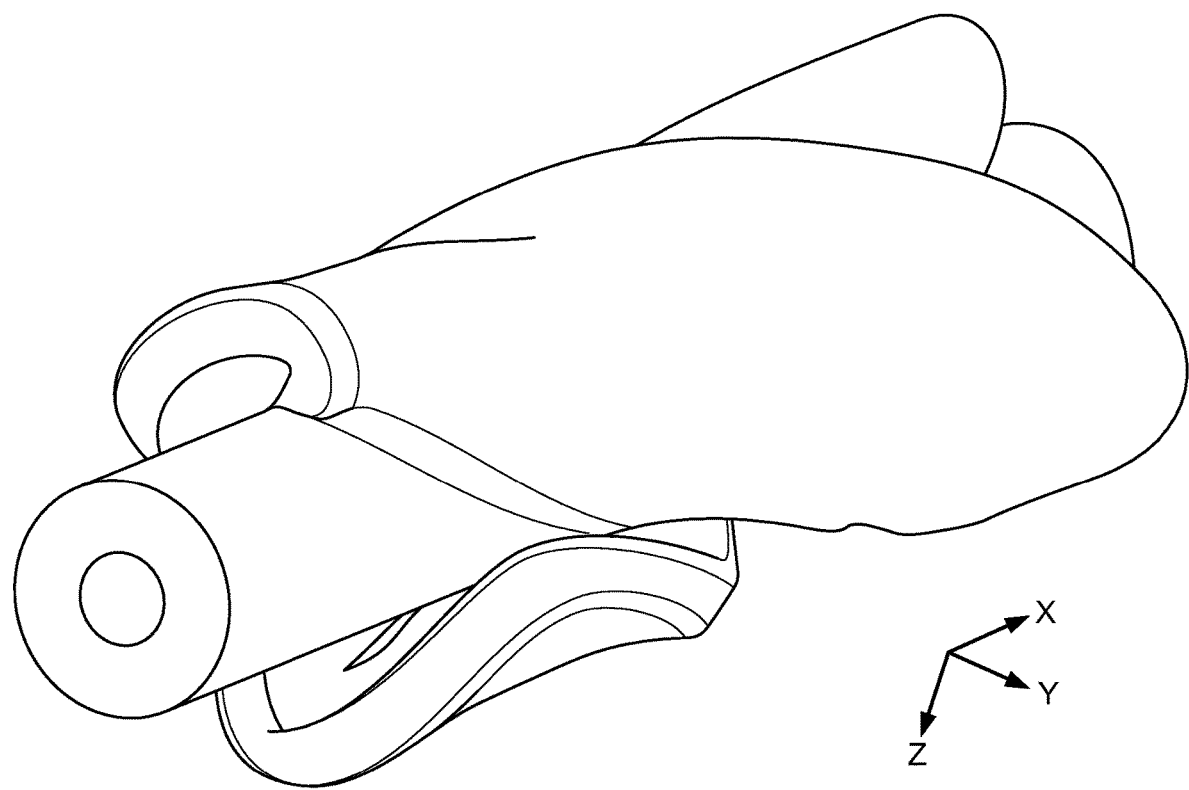
FIG. 9a the state A1 from FIG. 6.
Figure 9B:
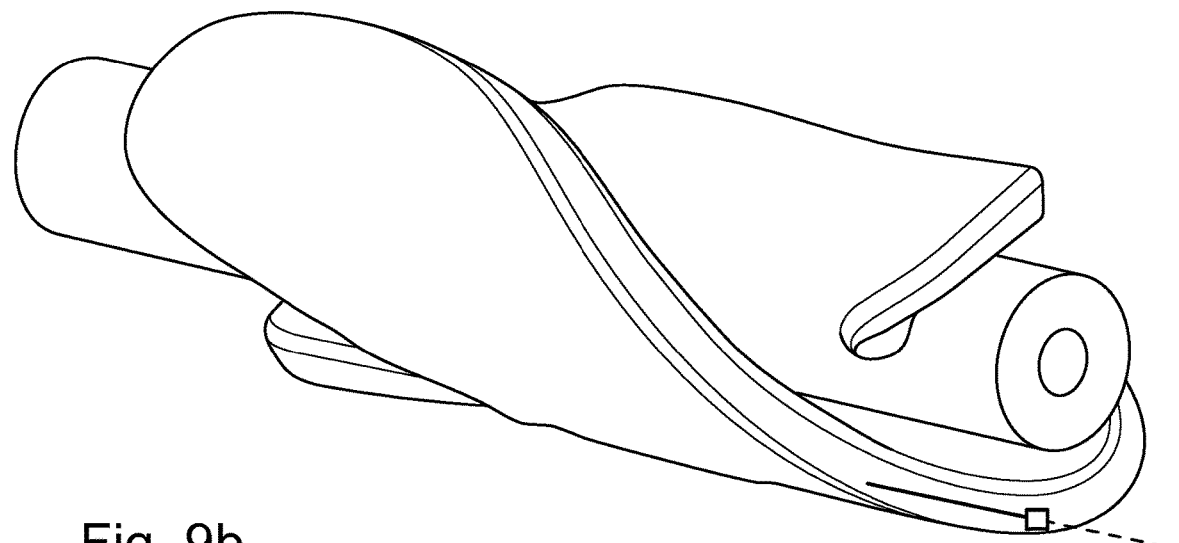
Figure 9C:
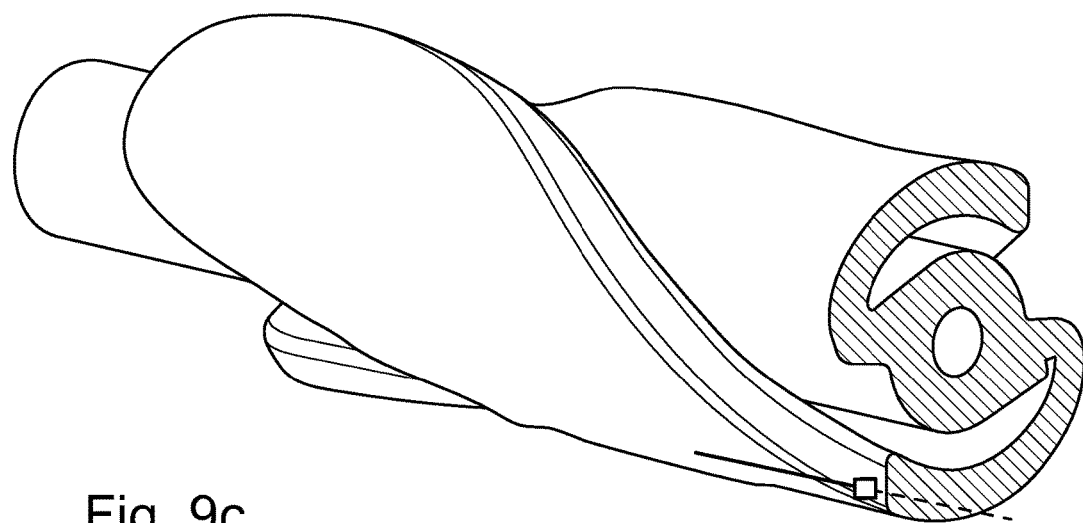
Figure 9H:
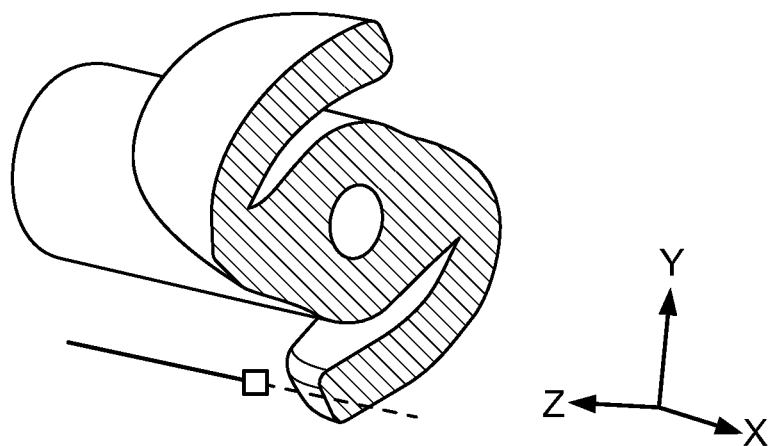

A compressed embodiment (first state "A1", see also FIG. 6) is shown in FIG. 9a. The x-axis is hereby shown in the direction of the rotor axis. With reference to the following Figures, the elastic comparative strain for example is disclosed (according to von Mises). Again, the above-mentioned single-blade rotor (the rotor blade is separated by the hub) is shown as rotor. FIGS. 9b-9h hereby show different sectional planes, it being expressed that the maximum comparative strains remain low due to the geometry chosen here, which leads to low-hysteresis and low-creep use.

Figure 10:
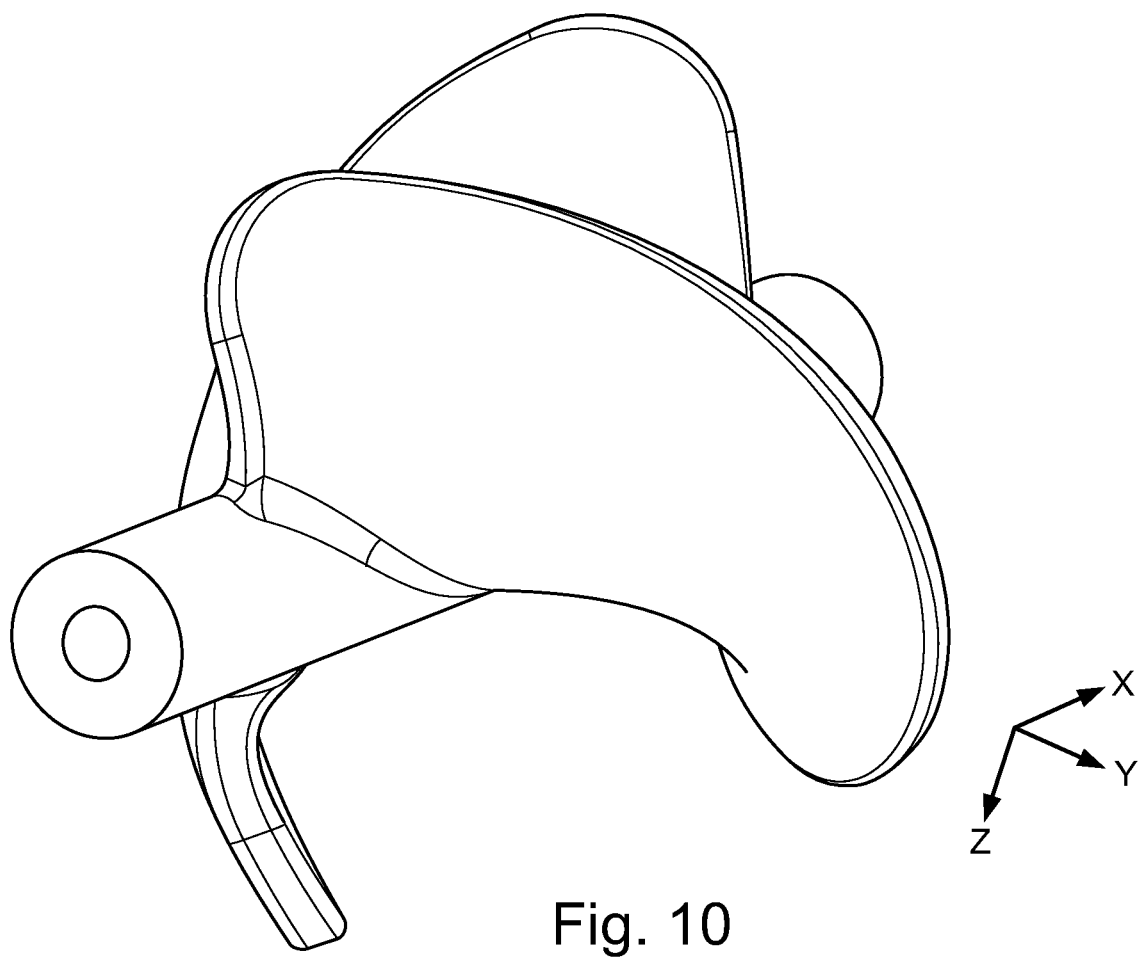

For comparison, once again the second state "A2" is shown in FIG. 10.

Figure 11:
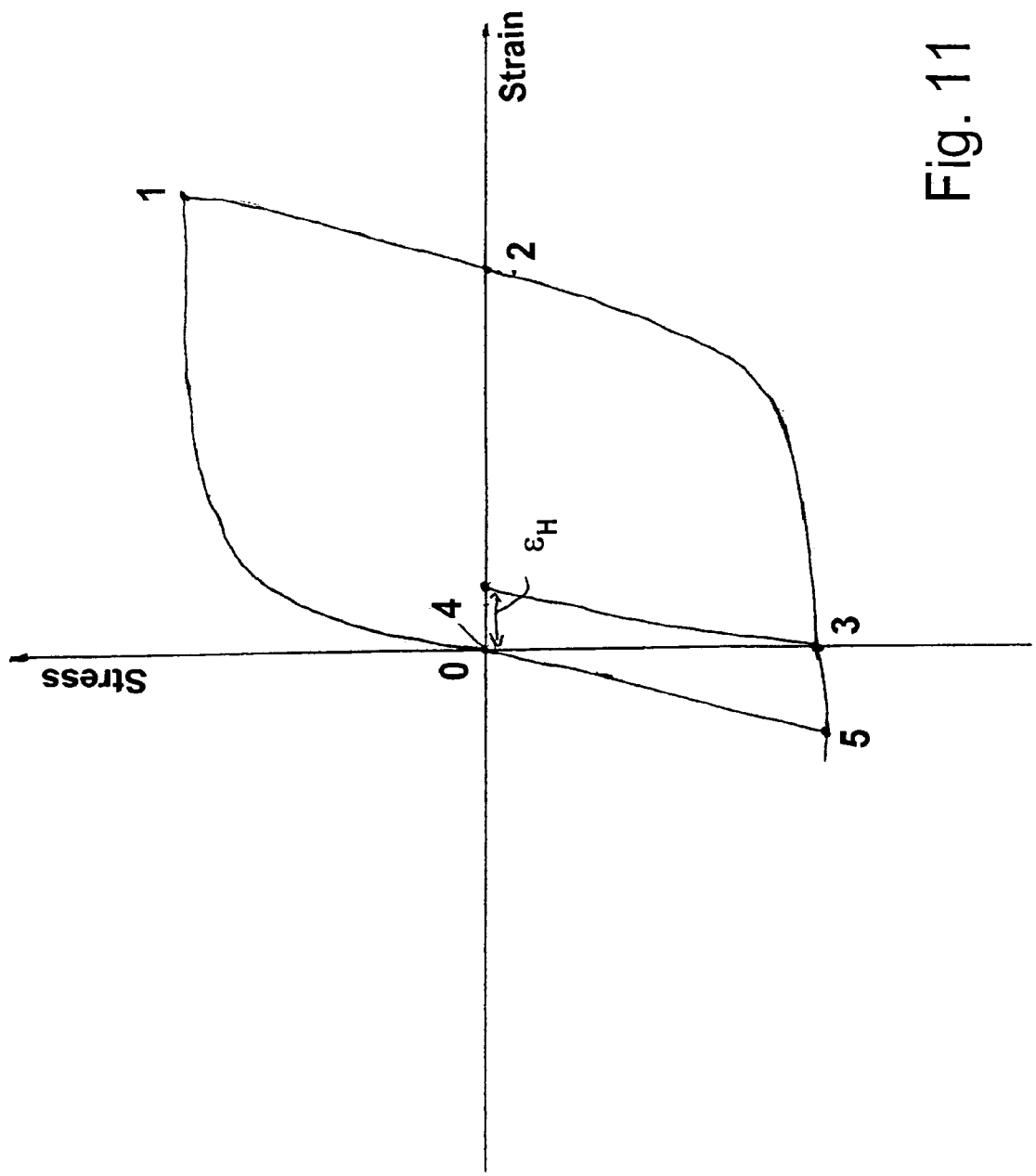

FIG. 11 shows a part of a typical hysteresis curve of a material which is unloaded again after a corresponding deformation. The point designated with "0" is the initial state of the unloaded workpiece. Point "1" corresponds to the point designated as compressed rotor. If the rotor is now unloaded at this point, i.e. the stress is reduced to zero, then a permanent deformation (point "2") remains in place, which here constitutes more than 50% of the maximum strain of the material in the compressed state. The rotor would therefore no longer adopt the original shape. Only by means of further loading counter to the original loading direction would the rotor again adopt its original shape (point "3"). This loading would have to produce material stresses which correspond, in their size, approximately to the original loading. The production of opposing stresses of this order of magnitude solely by the fluid pressure is however hardly realistic for a blood pump since then considerable damaging forces would act on the blood. During unloading in this state, the rotor would retain a permanent deformation (point "4"). Hence a state would be provided which produces non-repeatable conditions for handling of such a blood pump. Only by means of a further increase in these (negative) stresses is it possible to reach the point of the curve designated with "5" from which the initial state "0", in which the rotor adopts its initial form in the unloaded state, can be achieved again upon unloading.

Figure 12:
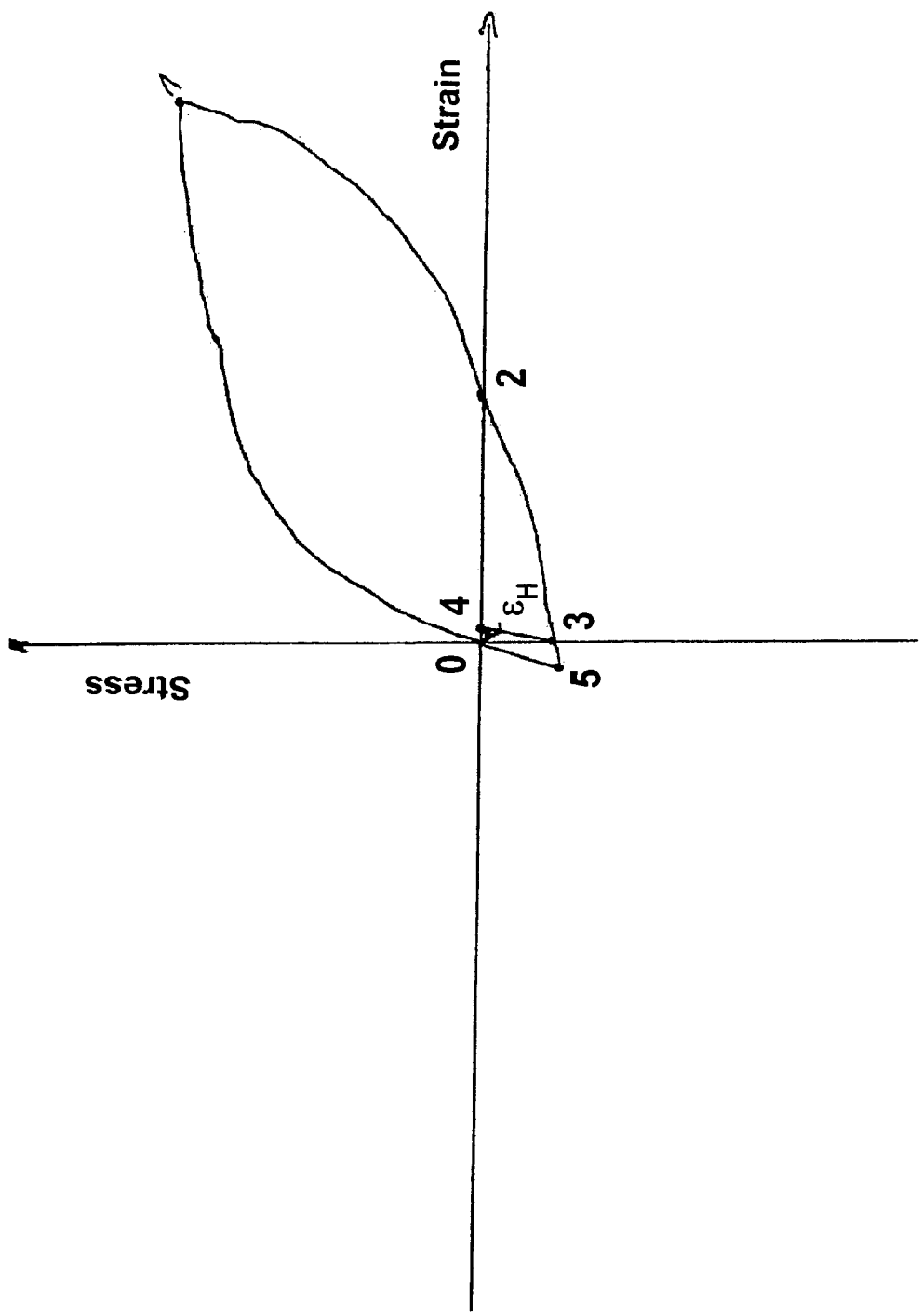

FIG. 12 shows the deformation behaviour of a material which shows relatively low hysteresis. Points "0" to "5" corresponding to the illustration in FIG. 11. Because of the lower permanent deformations, a controllable behaviour of the rotor would rather be producible here since the lower permanent deformations have fewer substantial or insubstantial effects on the behaviour in practice. However, a material which has absolutely no hysteresis and would follow the curve "0"-"1" even when unloaded is ideal for the application. Best of all, such a behaviour is achievable or almost achievable if the design is maintained in the region of Hooke's straight line. For reliable function of such a rotor it is therefore substantially more crucial that the material displays low-hysteresis, ideally hysteresis-free behaviour, in the region of the occurring deformations, than that the rotor has a change in the characteristic line increase. It is crucial in particular that the residual strain, after the compression has disappeared (point 2), constitutes less than 50%, preferably less than 25%, of the maximum strain of the material in the first state in the practically relevant time.

Figure 13:
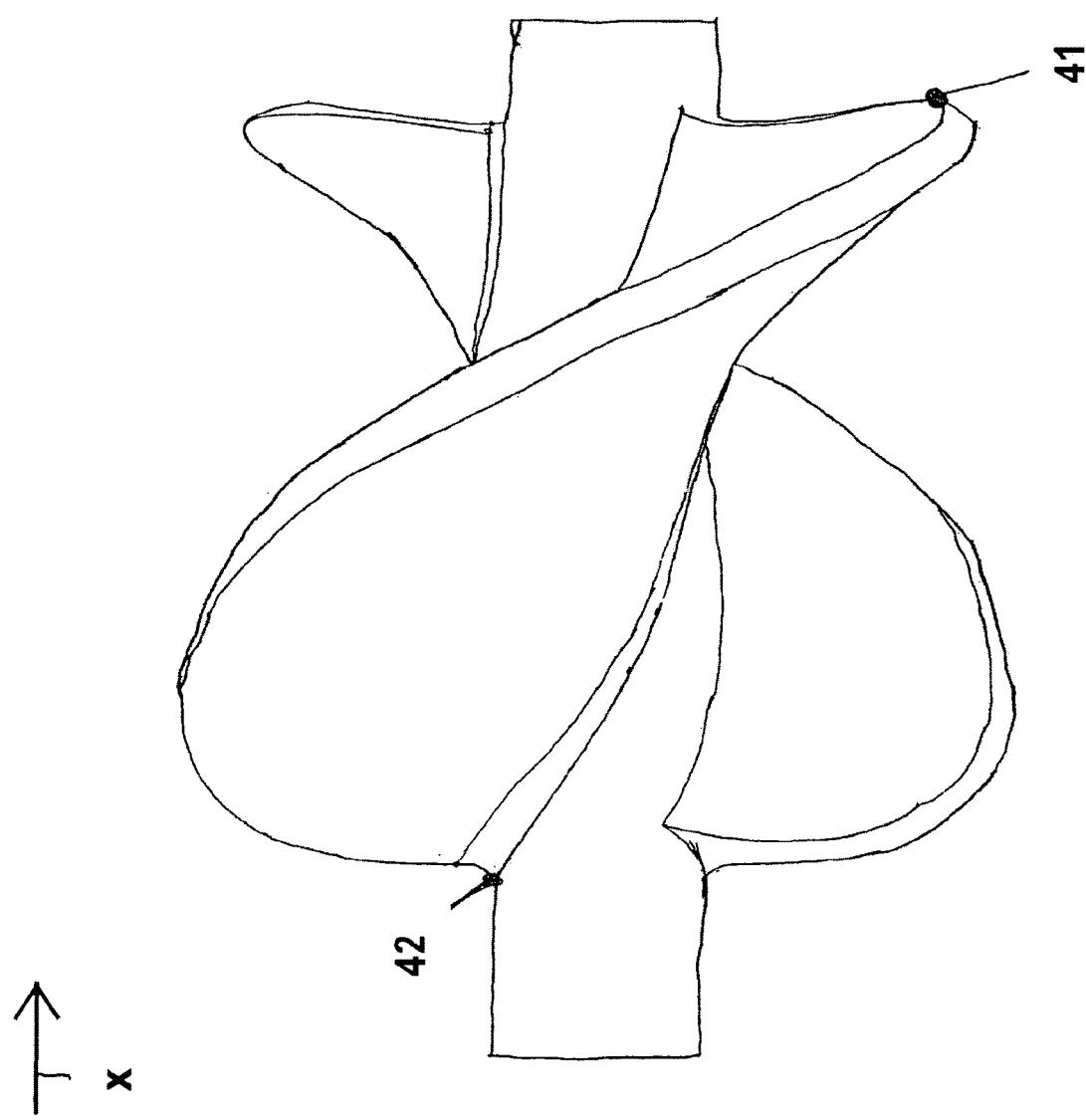
Figure 14:

FIGS. 13 and 14 illustrate the expanded and compressed state for a plastic material rotor.

FIG. 13 hereby shows an unmoving and force-free expanded state of the rotor, i.e. the rotor as it unfolds freely (without rotary movement) and not subjected to further loading by fluid counter-pressure.

FIG. 14 shows the same rotor in a radially compressed form, i.e. with radially folded-in blades. This state is that in which the rotor is introduced into the body compressed by means of at least one sheath; by withdrawing a sheath (or other means), the rotor in the heart or close to the heart is then brought into the radially expanded form (see FIG. 13).

It can hereby be seen that the hub of the rotor is essentially longitudinally stable. This is normal according to prior art, since the relatively solid hub shows essentially no lengthening/shortening due to application of the rotor blades.

Figure 15:
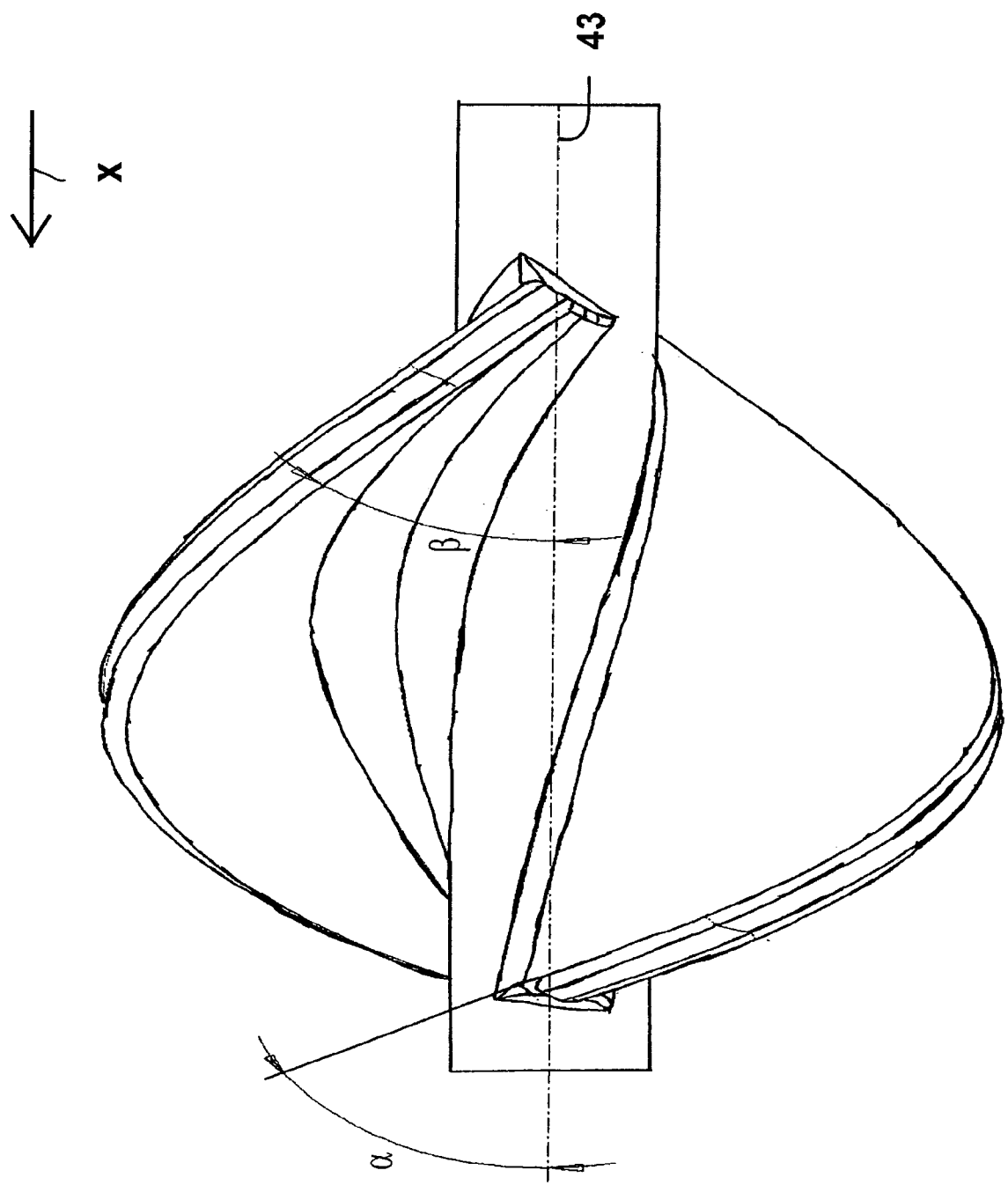

It should be noted that the "axial direction" mentioned below is the "x-direction" which is shown in FIGS. 13-15; this is generally in accord with the axis of rotation of the rotor.

However, it can be seen that, from the point, shown furthest left in the axial direction, of the blades 42/blade assembly/blade (in FIG. 13 on the left at the top, the point at which the transition from the constant diameter of the hub to the blade is effected), up to the point 41 situated furthest to the right (this is radially further out, as is evident by viewing FIG. 13) a lengthening is effected by means of compression. This is illustrated in FIG. 14. In FIG. 14, there is a clearly larger spacing from the point of the blade assembly 42' shown furthest left up to the point of the blade assembly 41' standing furthest right on the x-axis. This means that, by applying the rotor, a greater axial extension of the blade assembly/blade is provided. This is advantageous since good compressibility of the rotor, rotor blades/blades becomes possible with not too high forces and the volume of the rotor blades is distributed to a greater length, as a result of which a smaller diameter is adopted with the same volume. This is also caused by the fact that relatively good adaptation to a cylindrical shape is provided in the folded-in state. Lengthening is preferably, relative to the expanded initial state, at least 5%, in particular at least 10%.

This concept therefore stands out from existing concepts in which the axial extension of the blades does not vary between radially expanded and radially compressed state.

The above-described lengthening takes place, for example in the case of helically-shaped blades, also however in the case of blades disposed axially one behind the other. The effect is advantageous in particular also in the case of blades which have a gradient which changes over the rotor longitudinal axis since, as a result, local excessive strains are avoided.

In FIG. 15, there is represented by way of example a rotor in an operating state, i.e. the blade has deformed relative to the state represented in FIG. 13, such that the blade has been further deployed under the flow pressure in such a way that the blades are orientated essentially radially relative to the axis of rotation of the rotor. The illustrated angle α shows the angle which the rotor blade adopts at the blade exit relative to the axis. The illustrated angle β shows the angle which the rotor blade adopts at the blade entrance relative to the axis, the angle α in the illustrated example being approx. 40% greater than the angle β.

In the sense of the present application, the angles α or β are determined as follows.

As in particular can be seen from FIG. 15, the initial gradient of the blade (i.e. at the transition from the blade to the hub) is determined for the corresponding blade. The gradient of an end edge is hereby assumed, which, on the pressure side of the blade, represents the first end edge. This is shown by way of example in FIG. 15; the flow approach direction is effected in the x-direction (see arrow above on the right).

The same is true for the angle β which likewise is determined on the pressure side of the end edge; the corresponding tangent is applied to the initial region of this end edge, as shown in FIG. 15.

Generally, the mentioned tangents to the initial gradient will be skewed straight lines relative to the rotor central axis (represented in dot-dash lines in FIG. 15, see reference number 43). The angle determination is effected now such that the shortest possible distance between the two skewed lines is chosen; this can be determined mathematically unequivocally, in the case where the initial gradient tangent intersects the rotor central axis 43, this is the intersection point. If this is not the intersection point, then a parallel displacement along the previously determined shortest connection line is effected, until the two skewed straight lines intersect. Between these then intersecting straight lines, there are two angles, the smaller of the two angles is then α or β. In the sense of the present application, the angle α is 50° to 70.degree., preferably 55° to 65°. The angle β is 30° to 50°, preferably 36° to 44°.

The rotor blade has a continuous surface, the gradient between the entry angle and the exit angle following the function of a specific function (just as the unwinding of the gradient of a normal thread follows a straight line, the unwinding of the gradient of the blade preferably follows a parabola).

The parabola shape, in particular that of the quadratic parabola, has hereby proved advantageous, since the blood particles in contact with the rotor blade experience a constant uniform acceleration, which avoids acceleration peaks with correspondingly increased blood-damaging shear forces. In addition, the parabola shape leads to a blade which can be compressed readily in one direction, whereas it stabilises under flow pressure in the opposite direction.

In the sense of the present application, there is therefore understood by a parabola shape not a quadratic parabola ($y=ax^2+bx+c$) in the strict sense, but any shape which deviates from a straight line. Preferably this is a quadratic parabola (i.e. determinable by the term $y=ax^2+bx+c$, wherein the parameter x in this term is not necessarily the same as the x-direction shown in FIG. 15), it can however be also any function deviating from a straight line which can be described for example by a polynomial of a higher order.

For the individual blades, it applies however for the present application in every case that these should correspond in their "unwound" shape to such a non-straight shape. This applies in particular also for the case that a plurality of blades distributed over the length of the rotor is provided, i.e. not only the case, mainly observed in the Figures, of two blades which are oppositely situated distributed over the entire length of the rotor.

In the case of a cylindrical hub, the above-mentioned "unwinding" is relatively simple. Here, as mentioned, the corresponding line is observed preferably starting from the centre of the course of the blade (in the boundary region to the cylindrical hub).

This system applies slightly modified also for hub shapes which are not circular cylindrical, for example such as are shown in FIG. 3. For such conical, frustoconical and also convex, concave or bale-shaped (i.e. provided with spherical portions) hub geometries, the process is as follows.

Firstly, a line is drawn or modelled at the height of the hub surface (i.e. of the transition region from hub to blade) in the centre of the blade. A conical or bale-shaped structure is hereby produced (for example with reference to FIG. 3), on the surface of which a spiral is visible. For this spiral structure (this does not have to be a spiral in the mathematical sense, here it concerns merely an approximate circumscribing of the course of the line), thus for this line a stringing-together of the corresponding tangential planes along its course is undertaken. Along these tangential planes, there then occurs the imaginary rolling of the bale-shaped (conical) hub body. The line then arising in the plane should then in turn be non-straight, for example a quadratic parabola, as can be described by the function $y=ax^2+bx+c$.

Subsequently, the subjects of claims 16. ff. as originally filed, which represent patentable subjects per se, are explained once again in somewhat more detail. It hereby concerns firstly a rotor for a pump, having at least one blade, the rotor being able to be actuated to rotate about an axis of rotation in order to convey a fluid in the axial or radial direction, the rotor being deformable in the radial direction between a first, radially compressed state and a second, radially expanded state, and the blade having, in an operating state, an entry angle of the blade β and an exit angle of the blade α, the exit angle β deviating.

This aspect is very important and actually surprising. In the case of the blood or another body fluid to be conveyed, it indeed concerns an essentially incompressible fluid. Nonetheless however, due to the different angles α and β, i.e. by a change in the gradient of the blade (in the case of a plurality of blades: the blade assembly), an acceleration should be effected. It has been shown in lengthy experiments that this has a less-damaging effect on the blood. It is particularly advantageous to adopt the values set here in a compressible rotor (which thus can be pressed together in the radial direction) since, in this manner, also the pressed-together total volume can possibly be kept lower and also the rigidity behaviour of the rotor is more favourable, which permits smaller forces during compression with still high rigidity in the expanded state.

Advantageously, the blade has (either each individual blade or the one or two complete blades) a continuous surface. This means that here there are no "step-like" jumps.

This is particularly the case if no carrier structure is provided, i.e. if the plastic material is made of a uniform rubber or plastic material, possibly with partially hardened regions, but made of the same initial material, but also if support structures, if there are any, are embedded in such a manner that the impeller blade is not substantially thinner between these support structures than in the region of the support structures. As a result, very smooth surfaces are possible, which once again further reduce damage to the blood.

It is advantageous that, in a special embodiment, the angle α is greater than β. In such an embodiment the impeller blade is compressed very easily. When the rotor during compression is drawn into an enclosing sheath together with the pump housing or separately and, in being so drawn, is moved in x-direction (according to FIG. 15) vis-à-vis the mantle, the sheath thus receiving first that end of the rotor where the angle α is located, the deformation of the rotor during compression is such that no excessive, especially plastic, deformation occurs.

In specific areas of application or other embodiments it is advantageous that the angle α is smaller than the angle β. In such a design the impeller blade enters the fluid at an especially shallow angle so that minimized shear forces occur between rotor and fluid in this region. This causes especially slight damage to the blood in this region. Furthermore, such an embodiment is advantageous if the rotor during compression is inserted into a sheath, the rotor (with or without housing) thus moving against the x-direction (according to FIG. 15) vis-à-vis the sheath, the sheath thus receiving first that end of the rotor where the angle β is located.

A further embodiment provides that the gradient of the blade follows a parabola shape. The interpretation of the term "parabola" was effected as further back both for circular cylindrical hub bodies and conical hub bodies or bale-shaped hub bodies. What is important is that here above all the unwound central line in the "foot region" of the blade, i.e. towards the hub, does not represent a straight line, but rather a curved shape, preferably any parabola of a higher order, for particular preference one which can be described with the term $y=ax^2+bx+c$.

It should of course be understood that these embodiments mentioned in claims 16 to 20 as originally filed can be combined with all the features of claims 1 to 15 as originally filed; in order to avoid repetition, explicit repetition of the wording is therefore avoided.

The present application relates in addition to a pump comprising a housing and a rotor situated therein, the rotor having at least one blade, and the rotor being able to be actuated to rotate about an axis of rotation in order to convey a fluid in the axial or radial direction, the rotor being able to be deformed in the radial direction between a first, radially compressed state and a second, radially expanded state, and the blade being orientated essentially radially at the speed of rotation of the motor at which the power of the pump is at a maximum and/or the rotor at this speed of rotation having its maximum diameter.

The underlying idea is that the pump is generally designed from a design point at which the pump power is at its greatest; this speed of rotation can be in the range between 10,000 rotations per minute and 50,000 rotations per minute. What is now important is that, at this maximum speed of rotation, also the radial projection of the rotor is at its highest; in this way, it can be ensured that no "scratching" of the rotor on the housing is possible, i.e. with a corresponding design of the housing, indeed a pump gap can be minimised, though damage to the housing or the rotor is precluded. It is hereby advantageous that the blade points in essentially radial direction if this speed of rotation is reached; with elastic rotors, therefore a corresponding pre-curving in the non-moving but expanded state can be provided, so that at the highest speed of rotation (and the corresponding fluid counter-pressure) the blade then points radially outwards relative to the rotor axis.

The present application relates in addition to a pump according to one of the originally filed patent claims 1 to 25, there consequently being effected, between a radially compressed state and a radially expanded state of the rotor, a lengthening of the blade assembly, such that the maximum spacing between the most proximal point of the blade assembly and the most distal point of the blade assembly in the compressed state is at least 5%, preferably at least 10%, greater than the maximum spacing between the most proximal point of the blade assembly and the most distal point of the blade assembly in the expanded state.

These points are shown once again in FIGS. 13 and 14.

FIGS. 13 and 14 concern in principle the same rotor, which is however expanded in FIG. 13 (though not rotated), in FIG. 14 is compressed radially to the maximum (and likewise is not moved). The direction of the later flow is represented in FIGS. 13 and 14 by the arrow which is situated at the top on the left (x-direction). This means that the respectively left initial edge of the blade assembly engages firstly in the medium and conveyance in the x-direction (i.e. to the right) is effected. The most proximal point in the expanded state is designated with 41 and the most distal point with 42 (see FIG. 13 and by way of example the blade assembly there), i.e. the points 41 or 42 need not both be at the foot point of the blade and even not at the end point, any points are possible according to the blade geometry.

In the compressed state there is a different picture, see FIG. 14. There the spacing between the most proximal point (this time a different one, namely 41') and the most distal point 42' is shown (the latter remains in this embodiment at the same position, this does not however need to be so). The spacing between 41' and 42' is preferably at least 5%, particularly preferred at least 10%, greater than the spacing between 41 and 42 (i.e. in the expanded state, see FIG. 13 in this respect). The lengthening shown here is very favourable with respect to a minimisation of the volume in the compressed state. In particular in cooperation with the different angles α and β mentioned in claim 16 ff as originally filed, a form is hence produced which is designed to be flow-favourable and also volume-saving and can be folded together or radially compressed with low force. In particular in connection with the gradient according to the invention (i.e. non-straight unwinding), a hydraulically favourably designed rotor is produced.

The rotors shown in FIGS. 13-15 have respectively blades which uninterruptedly extend essentially over the length of the blading. The above embodiments however are valid correspondingly also for blade arrangements which are arranged axially one behind the other, see in particular FIG. 5 and the explanations there.

Aspects of the invention are inter alia:

1. Rotor (13) for a pump, having at least one blade (19, 20, 22, 29, 30, 31, 32), the rotor being actuated to rotate about an axis of rotation (21) in order to convey a fluid in the axial or radial direction, and the rotor being able to be deformed reversibly elastically in the radial direction between a first, radially compressed state and a second, radially expanded state.

2. Rotor according to aspect 1, characterised in that the rotor consists at least partially of a first, elastic material in the form of a foam polyurethane, a solid polyurethane, a thermoplastic elastomer, a rubber or a superelastic material, in particular superelastic polymer.

3. Rotor according to aspect 2, characterised in that the first material comprises a polyurethane based on a diisocyanate.

4. Rotor according to aspect 3, characterised in that the first material is produced with a polyether polyol.

5. Rotor according to aspect 3 or 4, characterised in that the first material is produced with an organically filled polyol, in particular a graft-, SAN- or polymer polyol or a PHD polyol.

6. Rotor according to aspect 2, characterised in that the first material is configured as a thermoplastic elastomer, in particular as polyamide TPE, as copolyester TPE, as styrene TPE, as urethane TPE or as thermoplastic elastomer with crosslinked rubber or comprises such a material.

7. Rotor according to aspect 2, characterised in that the first material is configured as natural or synthetic rubber, in particular as R-rubber, as M-rubber, as O-rubber, as Q-rubber, as T-rubber or as U-rubber or comprises such a material.

8. Rotor according to aspect 2 or one of the following, characterised in that the first material comprises at least one additive which mechanically reinforces the first material.

9. Rotor according to aspect 2 or one of the following, characterised in that the first material comprises an additive which makes the material mechanically anisotropic.

10. Rotor according to aspect 2 or one of the following, characterised in that the first material, by the production method of the rotor, has anisotropic mechanical properties.

11. Rotor according to aspect 2 or one of the following, characterised in that the first material has reinforcing fibres, in particular glass fibres, carbon fibres, plastic material fibres or natural fibres.

12. Rotor according to aspect 11, characterised in that the fibres are orientated according to a preferential direction.

13. Rotor according to aspect 2 or one of the following, characterised in that the first material is filled with nanoparticles.

14. Rotor according to aspect 1, characterised in that the rotor adopts the second state without the effect of external forces.

15. Rotor according to aspect 14, characterised in that the rotor which is initially actuated to rotate in the second state adopts a third state under fluid loading.

16. Rotor according to aspect 15, characterised in that the rotor is configured such that, during standstill, it returns from the third state reversibly elastically into the second state.

17. Rotor according to aspect 14 or 15, characterised in that the latter is configured such that adoption of the first state from the second state and adoption of the third state from the second state are effected in the opposite direction.

18. Rotor according to aspect 15, characterised in that the rotor, starting from the initial second state during transfer into the first state, subsequently into the third state and finally back into the second state, has a permanent residual strain ($\varepsilon_H$) of preferably less than 8%, particularly preferably less than 3%, very particularly preferred less than 1%. It is hereby assumed that the first state lasted for 0 hours to 12 hours and the third state lasted for 0 hours to 2,000 hours and the temperature was always between 1° C. and 50° C., preferably between 18° C. and 40° C.

19. Rotor according to one of the preceding aspects, characterised in that the rotor has at least one rotor blade, the rotor blade having a pressure side and a suction side and the pressure side having a monotonically convex cross-section.

20. Pump, in particular a blood pump, having a housing and a rotor according to one of the preceding aspects, characterised in that the interior of the housing is so large that the housing is not touched, in an expanded operating state even with maximum radial extension of the rotor, in particular with maximum deployment of conveyer elements, by the rotor, in particular not by a conveyor element.

21. Pump according to aspect 20, characterised in that the housing, in particular in the axial region in which the rotor has conveyor elements, delimits a cylindrical interior.

22. Intraventricular blood pump comprising a rotor according to one of the preceding aspects and also a sheath, this sheath being configured such that, during penetration of the rotor into the sheath, the rotor is compressed at least radially.

23. Method for providing an intraventricular blood pump according to aspect 22, characterised in that the sheath and rotor are provided initially unjoined and the rotor is introduced into the sheath only immediately before implantation in a human or animal body. The advantage: no settling of the materials, no adhesion of the rotor to the casing/sheath, function checking before implantation is possible, also, due to the short time, flow and hysteresis effects are minimised.

24. Rotor according to one of the aspects 1 to 23, characterised in that there is effected, between a radially compressed and a radially expanded state of the rotor, a lengthening of the blade assembly such that the maximum spacing between the most proximal point of the blade assembly and the most distal point of the blade assembly in the compressed state is at least 5%, preferably at least 10%, greater than the maximum spacing between the most proximal point of the blade assembly and the most distal point of the blade assembly in the expanded state.

25. Rotor according to one of the aspects 1 to 19, characterised in that at least one blade extends essentially over the length of the entire blading (blading assembly) or in that a plurality of blades which are distributed axially over the length of the blading/blade assembly is provided.

The invention claimed is:

1. A blood pump comprising:
a helical rotor blade configured to be rotated to convey a fluid through the blood pump, the helical rotor blade having a compressed state, a deployed state, and an operational state, and wherein the helical rotor blade is radially expanded in the operational state;
a housing surrounding the helical rotor blade, the housing including an expandable suction cage at a distal end of the housing and apertures at a proximal end of the housing, the apertures being proximal of the helical rotor blade; and
a rotor hub to which the helical rotor blade is coupled,
wherein the helical rotor blade is configured to expand from the deployed state to the operational state when rotated, such that the helical rotor blade has its maximum diameter in the operational state,
wherein a plurality of helical rotor blades are spaced apart from each other and distributed axially over a length of the rotor hub, and
wherein each of the plurality of helical rotor blades and the rotor hub are made of an elastic material, wherein the elastic material is selected from a foam polyurethane, a solid polyurethane, a thermoplastic elastomer, a rubber, a superelastic material, or superelastic polymer, and wherein the elastic material comprises a polyurethane based on a diisocyanate.

2. A blood pump comprising:
a helical rotor blade configured to be rotated to convey a fluid through the blood pump, the helical rotor blade having a compressed state, a deployed state, and an operational state, and wherein the helical rotor blade is radially expanded in the operational state;
a housing surrounding the helical rotor blade, the housing including an expandable suction cage at a distal end of the housing and apertures at a proximal end of the housing, the apertures being proximal of the helical rotor blade; and
a rotor hub to which the helical rotor blade is coupled,
wherein the helical rotor blade is configured to expand from the deployed state to the operational state when rotated, such that the helical rotor blade has its maximum diameter in the operational state,
wherein a plurality of helical rotor blades are spaced apart from each other and distributed axially over a length of the rotor hub, and
wherein each of the plurality of helical rotor blades and the rotor hub are made of an elastic material, wherein the elastic material is produced with a polyether polyol.

3. A blood pump comprising:
a helical rotor blade configured to be rotated to convey a fluid through the blood pump, the helical rotor blade having a compressed state, a deployed state, and an operational state, and wherein the helical rotor blade is radially expanded in the operational state;
a housing surrounding the helical rotor blade, the housing including an expandable suction cage at a distal end of the housing and apertures at a proximal end of the housing, the apertures being proximal of the helical rotor blade; and
a rotor hub to which the helical rotor blade is coupled,
wherein the helical rotor blade is configured to expand from the deployed state to the operational state when rotated, such that the helical rotor blade has its maximum diameter in the operational state,
wherein a plurality of helical rotor blades are spaced apart from each other and distributed axially over a length of the rotor hub, and
wherein each of the plurality of helical rotor blades and the rotor hub are made of an elastic material, wherein the elastic material is produced with an organically filled polyol selected from a graft-, SAN- or polymer polyol or a PHD polyol.

4. A blood pump comprising:
a helical rotor blade configured to be rotated to convey a fluid through the blood pump, the helical rotor blade having a compressed state, a deployed state, and an operational state, and wherein the helical rotor blade is radially expanded in the operational state;
a housing surrounding the helical rotor blade, the housing including an expandable suction cage at a distal end of the housing and apertures at a proximal end of the housing, the apertures being proximal of the helical rotor blade; and
a rotor hub to which the helical rotor blade is coupled,
wherein the helical rotor blade is configured to expand from the deployed state to the operational state when rotated, such that the helical rotor blade has its maximum diameter in the operational state,
wherein a plurality of helical rotor blades are spaced apart from each other and distributed axially over a length of the rotor hub, and
wherein each of the plurality of helical rotor blades and the rotor hub are made of an elastic material, wherein the elastic material is configured as a thermoplastic elastomer selected from a polyamide TPE, a copolyester TPE, a styrene TPE, a urethane TPE, or a thermoplastic elastomer with cross-linked rubber.

5. A blood pump comprising:
a helical rotor blade configured to be rotated to convey a fluid through the blood pump, the helical rotor blade having a compressed state, a deployed state, and an operational state, and wherein the helical rotor blade is radially expanded in the operational state;
a housing surrounding the helical rotor blade, the housing including an expandable suction cage at a distal end of the housing and apertures at a proximal end of the housing, the apertures being proximal of the helical rotor blade; and
a rotor hub to which the helical rotor blade is coupled,
wherein the helical rotor blade is configured to expand from the deployed state to the operational state when rotated, such that the helical rotor blade has its maximum diameter in the operational state,
wherein a plurality of helical rotor blades are spaced apart from each other and distributed axially over a length of the rotor hub, and
wherein each of the plurality of helical rotor blades and the rotor hub are made of an elastic material, wherein the elastic material is configured as a natural or synthetic rubber, wherein the natural or synthetic rubber is selected from R-rubber, M-rubber, O-rubber, Q-rubber, T-rubber, or D-rubber.

\* \* \* \* \*